US012801911B2

(12) United States Patent
Witzgall

(10) Patent No.: US 12,801,911 B2
(45) Date of Patent: Nov. 17, 2026

(54) DEEP RAPID CLASS AUGMENTATION

(71) Applicant: Leidos, Inc., Reston, VA (US)

(72) Inventor: Hanna Elizabeth Witzgall, Chantilly, VA (US)

(73) Assignee: Leidos Inc., Reston, VA (US)

( * ) Notice: Subject to any disclaimer, the term of this patent is extended or adjusted under 35 U.S.C. 154(b) by 1014 days.

(21) Appl. No.: 17/083,969

(22) Filed: Oct. 29, 2020

(65) Prior Publication Data

US 2021/0073637 A1 Mar. 11, 2021

(51) Int. Cl.

| | |
|---|---|
| ***G06N 3/08*** | (2023.01) |
| ***B01L 3/00*** | (2006.01) |
| ***G01N 1/02*** | (2006.01) |
| ***G01N 33/53*** | (2006.01) |
| ***G06F 16/55*** | (2019.01) |
| ***G06N 3/04*** | (2023.01) |

(52) U.S. Cl.

CPC .......... *G06N 3/08* (2013.01); *B01L 3/502715* (2013.01); *G01N 1/02* (2013.01); *G01N 33/5302* (2013.01); *G06F 16/55* (2019.01); *G06N 3/04* (2013.01); *B01L 2200/027* (2013.01); *B01L 2200/0689* (2013.01); *B01L 2200/10* (2013.01); *B01L 2300/04* (2013.01); *B01L 2300/0636* (2013.01); *B01L 2300/0809* (2013.01); *B01L 2300/123* (2013.01); *B01L 2300/126* (2013.01); *G01N 2001/028* (2013.01)

(58) Field of Classification Search

CPC ............. G06N 3/04; G06N 3/08; G06F 16/55

See application file for complete search history.

(56) References Cited

U.S. PATENT DOCUMENTS

| | | | | |
|---|---|---|---|---|
| 6,760,715 B1 * | 7/2004 | Barnhill | G16B 40/00 | 706/45 |
| 9,607,233 B2 * | 3/2017 | Kaizerman | G06V 10/774 | |
| 11,074,711 B1 * | 7/2021 | Akbas | G06V 10/454 | |
| 2008/0089591 A1 * | 4/2008 | Zhou | G06F 18/254 | 382/224 |
| 2010/0002929 A1 * | 1/2010 | Sammak | G06T 7/0014 | 382/133 |
| 2015/0120626 A1 * | 4/2015 | Gupta | G06N 3/08 | 706/20 |
| 2021/0073637 A1 | 3/2021 | Witzgall | | |

OTHER PUBLICATIONS

Rajasekar Venkatesan et. al "A Novel Progressing Learning Techniques for Multi-Class Classification", Neuro Computing 207, 2018, Elsevier Publications, (Year: 2018).*

(Continued)

*Primary Examiner* — Li B. Zhen
*Assistant Examiner* — Tirumale K Ramesh
(74) *Attorney, Agent, or Firm* — Dawn-Marie Bey; Bey & Cotropia PLLC

(57) ABSTRACT

Deep RCA uses a modified recursive least squares (RLS) optimization method and a novel null-class vector that together allow the algorithm to remember prior classes as it learns the new class. Deep RCA only has to be trained on the new class data which results in a significant improvement in training speed and almost no memory requirements to achieve the goal of near, real-time class augmentation for deep neural networks.

5 Claims, 20 Drawing Sheets

(56) References Cited

OTHER PUBLICATIONS

R. Venkatesan and M.J. Er, "A Novel Progressive Learning Technique for Multi-class Classification", arXiv:1609.00085v1, Sep. 1, 2016.
R. Venkatesan and M.J. Er, "A Novel Progressive Learning Technique for Multi-class Classification", arXiv:1609.00085v2, Jan. 22, 2017.
G.B. Huang, L. Chen, "Extreme Learning Machine: A New Learning Scheme of Feedforward Networks", Proceedings of International Joint Conference on Neural Networks, vol. 2, pp. 985-990, 2004.
G.B. Huang, L. Chen, C.K. Siew, "Universal Approximation Using Incremental Construction Feedforward Networks with Random Hidden Nodes", IEEE Transactions on Neural Networks, vol. 17, No. 4, pp. 879-892, 2006.
Chuangi Tan, Fuchun Sun, Tao Kong, Wenchang Zhang, Chao Yang, Chunfang Liu, "A Survey on Deep Transfer Learning," arXiv:1808.01974, Aug. 6, 2018.
LeCun, Yann; Cortez, Corinna; Burges, Christopher C.J., "*The MINIST Database of Handwritten Digits*" [online] [retrieved Oct. 29, 2020], 7 pp., Retrieved from the Internet: yann.lecun.com/exdb/mnist/.
W.H. Hager. "Updating the inverse of a matrix," SIAM Review, 31(2):221-239, Jun. 1989.
J. Howard, "Imagenette" [online], [retrieved on Oct. 29, 2020], Retrieved from the Internet: https://github.com/fastai/imagenette.
"Python vs. R for Artificial Intelligence, Machine Learning, and Data Science," by Scenario or Task by Alex Castrounis of Innoarchitech, published online by O'Reilly Media, Copyright InnoArchiTech LLC 2020 [retrieved on Oct. 16, 2020], Retrieved from the Internet: https://www.innoarchitech.com/blog/python-vs-or-r-artificial-intelligence-ai-machine-learning-data-science-which-use, 27 pp.
"Production vs Development Artificial Intelligence and Machine Learning," by Alex Castrounis of Innoarchitech, published online by O'Reilly Media, Copyright InnoArchiTech LLC 2020 [retrieved on Oct. 16, 2020], Retrieved from the Internet: https://www.innoarchitech.com/blog/development-vs-or-production-batch-offline-online-automated-artificial-intelligence-ai-machine-learning, 24 pp.
"Advanced Analytics Packages, Frameworks, and Platforms," by Alex Castrounis of Innoarchitech, published online by O'Reilly Media, Copyright InnoArchiTech LLC 2020 [retrieved Oct. 16, 2020], Retrieved from the Internet: https://www.innoarchitech.com/blog/packages-frameworks-platforms-by-scenario-task-artificial intelligence-ai-machine-learning-data-science, 29 pp.
H. Witzgall, "Rapid Class Augmentation For Continuous Deep Learning Applications," International Conference on Machine Learning Applications (ICMLA), 2020.
M. Arif Wani, et al., "Advances in Intelligent Systems and Computing," vol. 1395, Deep Learning Applications, vol. 3, Springer, Copyright 2022.
Tsung-Yi Lin, et al., "Microsoft COCO: Common Objects in Context," arXiv: 1405.0312v3, Feb. 21, 2015.
H. Witzgall, "Deep Rapid Class Augmentation: A New Progressive Learning Approach that Eliminates the Issue of Catastrophic Forgetting," Deep Learning Applications, vol. 3, Springer, Oct. 2021.
S.-A. Rebuffi, A. Kolesnikov, G. Sperl, and C. H. Lampert, "icarl: Incremental classifier and representation learning," in CVPR, 2017, pp. 2001-2010. (iCARL Replay).
H. Shin, J. K. Lee, J. Kim, and J. Kim, "Continual learning with deep generative replay," in NeurIPS, 2017, pp. 2990-2999.
C. Fernando, D. Banarse, C. Blundell, Y. Zwols, D. Ha, A. A. Rusu, A. Pritzel, and D. Wierstra, "Pathnet: Evolution channels gradient descent in super neural networks," arXiv preprint arXiv:1701.08734, 2017.
Ren, B.; Wang, H.; Li, J.; and Gao, H. 2017. Life-long learning based on dynamic combination model. Applied Soft Computing 56:398-404.
J. Kirkpatrick, R. Pascanu, N. Rabinowitz, J. Veness, G. Desjardins, A. A. Rusu, K. Milan, J. Quan, T. Ramalho, A. GrabskaBarwinska et al., "Overcoming catastrophic forgetting in neural networks," PNAS, p. 201611835, 2017. (EWC regularization).
C. V. Nguyen, Y. Li, T. D. Bui, and R. E. Turner, "Variational continual learning," arXiv preprint arXiv:1710.10628, 2017. (VCL).
Z. Li and D. Holem, "Learning without Forgetting", https://arxiv.org/abs/1606.09282, Feb. 2017 (LwF).
K. Shmelkov, C. Schmid, and K. Alahari, "Incremental learning of object detectors without catastrophic forgetting," in ICCV, 2017, pp. 3400-3409.
A. Rannen, R. Aljundi, M. B. Blaschko, and T. Tuytelaars, "Encoder based lifelong learning," in ICCV, 2017, pp. 1320-1328.
Zixuan Ke1 , Bing Liu1 , Nianzu Ma1 , Hu Xu2 and Lei Shu3, "Achieving Forgetting Prevention and Knowldege Transfer in Continual Learning", NeuralPS 2021.
H.Jung, J.Ju, M.Jung and J.Kim, "Less-forgetting Learning in Deep Neural Networks", https://arxiv.org/abs/1607.00122, Jul. 2016.
M. De Lange, R. Aljundi, M.Masana, S. Parisot, X. Jia, A. Leonardis, G. Slabaugh, T. Tuytelaars, A continual leraning survey: Defying forgetting in classification tasks, Apr. 2021, https://arxiv.org/pdf/1909.08383.pdf (University of Kansas).
R. Kemker, M. Mclure, A. Abinto, T. Hayes, C. Kanan, "Measuring Catastrophic Forgetting in Neural Networks", Nov. 2017, https://arxiv.org/pdf/1708.02072.pdf (Rochester Institute of Technology).
Mathilde Caron, Hugo Touvron, Ishan Misra, Herve Jegou, Julien Mairal, Piotr Bojanowski, Armand Joulin, "Emerging Properties in Self-Supervised Vision Transformers", May 2021, arXiv:2104.14294v2.
Alexey Dosovitskiy, Lucas Beyer, Alexander Kolesnikov, Dirk Weissenborn, Xiaohua Zhai, Thomas Unterthiner, Mostafa Dehghani, Matthias Minderer, Georg Heigold, Sylvain Gelly, Jakob Uszkoreit, Neil Houlsby, "An Image is Worth 16x16 Words: Transformers for Image Recognition at Scale", Jun. 2021, arXiv:2010.11929.
H. Witzgall, "Jointly Optimal Incremental Learning with Self-Supervised Vision Transformers", Submitted to IEEE Aerospace Conference, 2024.
T. Hastie, R. Tibshirani, J. Friedman, The Elements of Statistical Learning, Springer Series in Statistics. New York: Springer-Verlag, 2001.
Li, Y., Mao, H., Girshick, R. and He, K., Oct. 2022. Exploring plain vision transformer backbones for object detection. In European conference on computer vision (pp. 280-296). Cham: Springer Nature Switzerland.
Vaswani, A., Shazeer, N., Parmar, N., Uszkoreit, J., Jones, L., Gomez, A.N., Kaiser, L. and Polosukhin, I., 2017. Attention Is All You Need.(Nips), 2017. arXiv preprint arXiv:1706.03762, 10, p. S0140525X16001837.
J. Jang, S. Ye, S. Yang, J. Shin, J. Han, G. Kim, S. Jungkyu Choi, M. Seo, 'Towards Continual Knowledge Learning of Language Models', May 2022, https://arxiv.org/pdf/2110.03215.pdf.
M. Biesialska, K.a Biesialska, M. R. Costa-jussa, 'Continual Lifelong Learning in Natural Language Processing: A Survey' Proceedings of the 28th International Conference on Computational Linguistics, pp. 6523-6541 Barcelona, Spain (Online), Dec. 8-13, 2020; https://aclanthology.org/2020.coling-main.574.pdf.
Tongtong Wu, Massimo Caccia, Zhuang Li, Yuan-Fang Li, Guilin Qi, Gholamreza Haffari, 'Pretrained Language Model in Continual Learning: A Comparative Study', International Conference on Learning Representations (ICLR) May 2022, https://researchmgt.monash.edu/ws/portalfiles/portal/470247539/466809118_oa.pdf.
Jacob Devlin Ming-Wei Chang Kenton Lee Kristina Toutanova, 'BERT: Pre-training of Deep Bidirectional Transformers for Language Understanding', May 2019; https://arxiv.org/pdf/1810.04805.pdf.
Victor Sanh, Lysandre Debut, Julien Chaumond, Thomas Wolf, 'DistilBERT, a distilled version of BERT: smaller, faster, cheaper and lighter', Mar. 2020; https://arxiv.org/pdf/1910.01108.pdf.
BBC News Archive dataset for topic classification; https://www.kaggle.com/datasets/hgultekin/bbcnewsarchive (retrieved Sep. 8, 2024).
CoNLL Named-Enity-Recognition dataset https://paperswithcode.com/dataset/conll-2003 (retrieved Sept. 6, 2024).

* cited by examiner ne=number of epochs

Stage 1 (Epoch=0)

Stage 2 (Epoch=100)

Stage 3 (Epoch=300)

Stage 1 (Epoch=0)

Stage 2 (Epoch=100)

Stage 3 (Epoch=300)

DEEP RAPID CLASS AUGMENTATION

GOVERNMENT RIGHTS

This invention was made with government support under the NRO's ANALYSE contract no. CRN 328182. The government has certain rights in the invention.

CROSS-REFERENCE TO RELATED APPLICATION

The present application claims benefit of priority to U.S. Provisional Patent Application No. 62/888,134, entitled "DEEP RAPID CLASS AUGMENTATION" filed on Nov. 5, 2020.

BACKGROUND

Field of Embodiments

The embodiments are generally directed to progressive learning algorithms for use in rapid augmentation of a deep neural network classifier with new classes in a near-real-time.

Description of Related Art

An issue with current machine learning (ML) algorithms is that they generally require a large amount of training data and therefore a significant time to train. These long-training times makes most ML algorithms ill-suited for continuous learning applications where one would like to augment existing models with new classes on-the-edge and on-the-fly.

Of particular interest are deep neural networks' (DNN) for image classification and DNN's increasing viability for automating perception tasks. Much of DNN's effectiveness can be attributed to their ability to identify pertinent classification features from raw, high-dimensional sensor data. However, a major drawback of DNN classifiers is that finding these robust features often requires large amounts of training data and long training times. This currently inhibits the practical application of augmenting an existing DNN with new classes on-the-fly and in near real-time.

Both transfer and progressive learning techniques have been explored to address continuous learning applications, wherein one would like to augment existing models with new classes. Transfer learning is a well-known ML technique that is used to reduce the amount of data and the time required to train a DNN for a new classification task. The idea behind transfer learning is to reuse the feature weights that have been previously trained to map the raw data (e.g. images) to useful classification features learned from a previous dataset and task and apply them to a new classification task. This knowledge transfer can be implemented by freezing the feature weights that have been previously learned, up to but not including the model's final classification layer. In transfer learning, these old classification weights are then discarded and a new classification layer/network is built on top of the old feature extraction network. This new classification layer is usually randomly initialized and then trained for the new classification task. Because transfer learning freezes the core feature extraction layers, it significantly reduces the number of trainable parameters for the new network. This dramatically speeds up the training process and reduces the amount of data that is required to learn the new classification task while preventing overfitting.

Progressive learning is a research area that seeks to reduce the training time required to augment an existing model with additional new classes by reusing the knowledge gained from previously trained feature and classification weights. The classification knowledge transfer is done by reusing the previously learned weights for initialization of the old class weights in the newly augmented model. The new class weights are initialized randomly and usually scaled to match the mean of the old weight values. This newly initialized augmented classifier is then re-trained to learn the new class using the standard stochastic gradient descent (SGD) method. Note that in this training process, both the old and the new classification weights will be modified from their initial values to jointly optimize performance across all classes. The intent is that by initializing the classifier using the previously trained classification weights, the classifier will be closer to the final optimal solution because it avoids having to relearn low level features that are common across many classification tasks, which will result in quicker training convergence than random initialization.

Note that progressive learning differs from transfer learning in that progressive learning's objective is to augment an existing model with new classes rather than to build an entirely new classifier based on just the 'transferred' features. This distinction results in progressive learning approaches reusing both the feature weights and the previously learned classification weights rather than discarding the classification layer completely as is typically done in transfer learning. This allows progressive learning approaches to build multi-class models faster than if the final classification layer is completely discarded before retraining. By combining transfer learning's pre-trained feature extraction properties with progressive learning's pre-trained classifier, the time required to augment a large multi-class classifier can be significantly reduced and is more efficient than just using transfer learning alone. Note that unlike transfer learning, progressive learning does not freeze classification weights.

A drawback of current progressive learning approaches is that SGD requires retraining the model on data from all classes in order to jointly optimize the performance. This is because the ubiquitous SGD algorithm has no feature memory. For continuous learning applications, this choice of optimization is especially problematic because it forces the algorithm to constantly retrain its old class weights with previously-seen data while it learns the new class weights. Although this constant retraining avoids sub-optimal performance on the augmented classification task, it inhibits rapid progressive learning. Lack of memory is especially detrimental when augmenting large multi-class models because it requires the training to simultaneously learn a new class while constantly refreshing its knowledge over the large number of all the old classes.

For example, it might take weeks to train a classifier on the million-plus images in the ImageNet data set with 1,000 class labels. Now suppose new training data becomes available with two new class labels, and one would like to build a new classifier for all 1,002 classes. Current transfer learning approaches are highly inefficient because the transfer learning process learns only new class weights and labels and discards all memory of the 1,000 previous classes (although the model does remember its past feature embeddings). Thus, one is left with the unsatisfying options of either retraining for weeks (e.g., on a single GPU or training faster but at a much higher computational hardware expense) to build a new, 1,002-class model or to end up with the two different classifiers identifying different targets. A much more computationally efficient approach would be to preserve the knowledge of the transfer model's old class labels and weights during the process of learning the new feature weights. Such an architecture would significantly reduce the computational costs of training and augmenting a classifier's target classes. These identified learning inefficiency serve as the motivation to develop a new optimization approach for progressive learning that remembers previously seen correlations so that it won't forget the old classes as it is taught the new ones.

SUMMARY OF CERTAIN EMBODIMENTS

In a first exemplary embodiment herein, a computer-implemented process for augmenting a classification model for classifying received data into a correct class, includes: augmenting an initial classification model having n classes trained on old class data to include a new class c; and initializing training of an augmented classification model having n+c classes on training data consisting solely of new training data to new class c, wherein a classification accuracy of the n classes is maintained after training the augmented classification model on only the new class c training data.

In a second exemplary embodiment herein, at least one computer-readable medium storing instructions that, when executed by a computer, perform a method for augmenting a classification model for classifying received data into a correct class, includes: augmenting an initial classification model having n classes trained on old class data to include a new class c; and initializing training of an augmented classification model having n+c classes on training data consisting solely of new training data to new class c, wherein a classification accuracy of the n classes is maintained after training the augmented classification model on only the new class c training data.

In a third exemplary embodiment herein, a computer-implemented process for augmenting a classification model for classifying received non-linear, high dimensional data into a correct class, includes: a feature extractor for transforming non-linear, high dimensional data training data into linearly separable features prior to training an initial classification model having n classes; augmenting an initial classification model having n classes trained on old class data to include a new class c; and initializing training of an augmented classification model having n+c classes on training data consisting solely of new training data to new class c, wherein a classification accuracy of the n classes is maintained after training the augmented classification model on only the new class c training data.

BRIEF DESCRIPTION OF THE FIGURES

The following figures are intended to be considered along with the Detailed Description set forth below:

FIGS. 1(*b*) and 1(*c*) provide overviews of a prior art architecture;

DETAILED DESCRIPTION

Figure 1A:
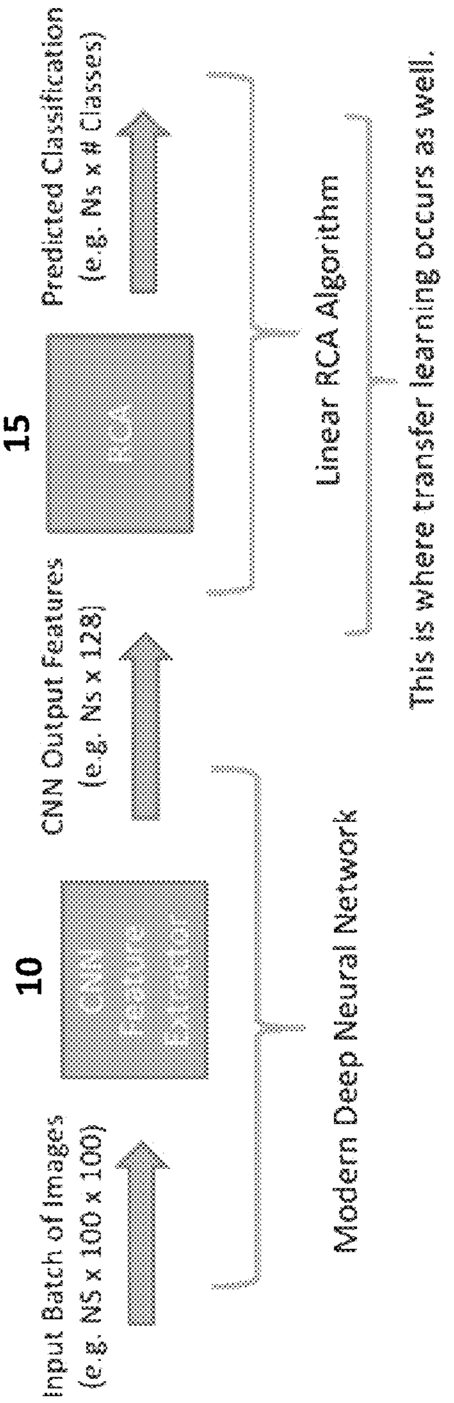
FIG. 1(*a*) provides a high level overview of a Deep RCA architecture described in one or more embodiments herein.

Motivated by a recognized need in the art to provide near-real time model augmentation capabilities, the present embodiments are directed to a new progressive learning approach called Deep Rapid Class Augmentation (Deep RCA). Deep RCA uses a modified recursive least squares (RLS) optimization method and a novel null-class vector that together allow the algorithm to remember prior classes as it learns the new class. This means Deep RCA only has to be trained on the new class data which results in a significant improvement in training speed and almost no memory requirements. The embodiments described herein have the potential to achieve the goal of near, real-time class augmentation for deep neural networks.

The roots of Deep RCA are found in the Progressive Extreme Learning Machine (ELM) algorithm that introduced the idea of using a modified RLS optimization approach for progressive learning which is described in R. Venkatesan et al., "A Novel Progressive Learning Technique for Multi-class Classification" arXiv: 1609.00085v1 and arXiv:1609.00085v2 (Sep. 1, 2016 and Jan. 22, 2017), which are incorporated herein by reference in their entirety. In particular, Progressive ELM, an online RLS implementation that adaptively updates its weights as new data becomes available, can be considered a model that has not yet seen any positive training examples for all of its future new classes.

Deep RCA builds upon this insight and introduces two important differences. The first difference is that Progressive ELM uses the ELM approach to detangle non-linearly separable input data into a linearly separable feature space, while Deep RCA will use a CNN (convolutional neural network). The key idea behind the original (non-progressive) ELM algorithm is to project the input data into a much higher dimensional and randomly selected feature space, with the intention that the high dimensionality will separate the non-linearly separable input data into a set of linearly separable features upon which a linear classifier will work as described by G. B. Huang, et al. in "Extreme Learning Machine: A New Learning Scheme of Feedforward Networks", Proceedings of International Joint Conference on Neural Networks, vol. 2, pp. 985-990, 2004 and "Universal Approximation Using Incremental Construction Feedforward Networks with Random Hidden Nodes", IEEE Transactions on Neural Networks, vol. 17, pp. 879-892, 2006. This general principal has been shown to work well for some applications and can significantly reduce the computation compared with the more modern deep learning algorithms. However, ELM does not work well when it must operate on high-dimensional input data, which is characteristic of most image data. This is because ELM must project this high dimensional data into a much higher dimensional feature space to achieve the linear separation. This results in the ELM prediction layer having to operate on and invert a feature matrix with potentially hundreds of thousands or millions of features, which is either infeasible or significantly slows computation. This limitation motivated the Deep RCA development to use the feature extraction capabilities of a deep neural network that seeks to find an optimum (non-random), lower dimensional feature subspace that can still linearly separate the feature classes.

The second difference between the progressive ELM algorithm and Deep RCA is an algorithmic modification to the initialization of a new class augmentation weight vector. Deep RCA specifies a new null class vector that is used to initialize a new class weight vector and can be updated whenever new data arrives, similarly to RLS inverse feature covariance. By specifically computing the null-class weight vector for each batch (or sample) of new data, one can initialize the new class vector without ever having to access the old class data in order to provide the negative new class examples. This means that RCA can progressively learn new classes without ever having to store the old class data, other than what is stored in the inverse feature covariance and the new, null class vector. This allows all the class data to be discarded after training while still allowing the model to be augmented in the future. Recall that SGD requires access to samples from of all training classes for class augmentation and so all training data must be preserved to further augment that model. Furthermore, it will be shown that this null-class vector can be computed directly from the old class weights. Thus, there will be no requirement for preserving old training data to compute the null-class vector as was previously required.

The combination of RCA's new null-class weight vector, along with the features extracted from a CNN, make RCA very memory efficient. Deep RCA is the first progressive algorithm that can reliably and deterministically augment new classes without requiring access to the old training data. This be a significant advantage for platforms on the edge that want to augment their classifiers with new classes but do not want to store all the previous class training data. Additionally, the training will be even faster than traditional progressive algorithms (which are already much faster than retraining from scratch) because the weight updates only need to be run on the new class data rather than having to update the weights from all the classes on the training data from all the classes.

Figure 1B:
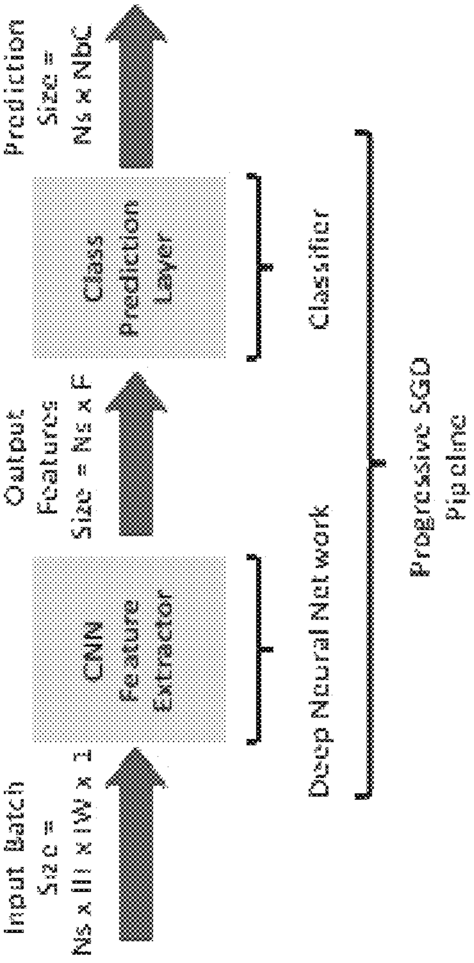
FIGURE 1(b) Prior Art
Figure 1C:
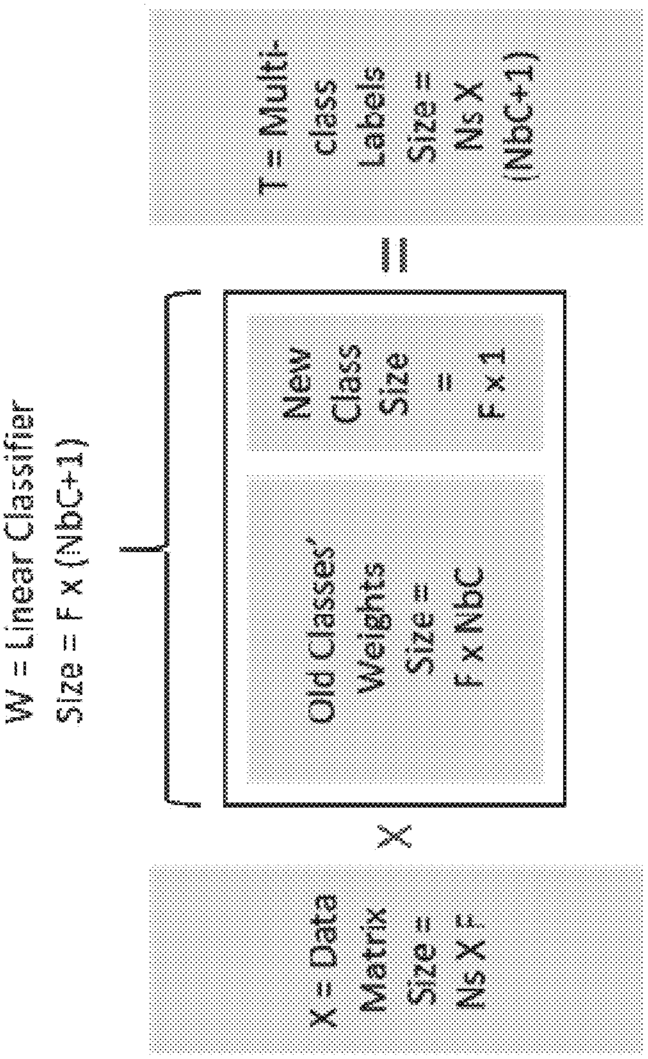
FIGURE 1(c) Prior Art

FIG. 1(*a*) provides a high level overview of the Deep RCA architecture. A CNN 10 is used to detangle the high dimensional data (e.g. imagery) into a much lower dimensional space where the transformed class features are ideally linearly separable. Next, an RCA classifier 15 is used on the features extracted from a CNN. More detailed descriptions and comparisons are provided below exemplifying improvements over existing methodologies.

Initially, the RCA classifier is trained using a modified version of the recursive least squares (RLS) algorithm. Recall that RLS is a recursive implementation of the well-known normal equation that was designed to create a computationally efficient online-training method for adapting a linear model to changing data statistics. The normal equation's closed form minimum-mean-square-error (MMSE) solution to the linear set of equations Xw=T, where X is the Ns×F data matrix, w is the linear prediction model and T is the multi-class label matrix of shape Ns×NbC, is $$w = (XX^T)^{-1}X^T T. \tag{1}$$

The RLS algorithm uses the matrix inverse lemma to provide a recursive method to compute the normal equation's inverse feature covariance matrix, $M=(XX^T)^{-1}$ as shown:

$$M_{k+1} = M_k - M_k x_{k+1}^T (1 + x_{k+1} M_k x_{k+1}^T)^{-1} x_{k+1} M_k \tag{2}$$

Note that when $x_{k+1}$ represents a single feature vector, the inverse function operates on a scalar value. In general, the size of the matrix inverse in Eq. (3) is determined by the batch size of $x_{k+1}$ which allows one to control the complexity of the inverse operation to manageable levels.

The model w can now be updated recursively at time step k+1 using $$w_{k+1} = w_k + \lambda M_{k+1} x_{k+1} (t_{k+1} - x_{k+1} w_k), \tag{3}$$

where $t_{k+1}$ is the multi-class label vector for the k+1th sample. For the model augmentation application, we want to preserve memory (and not adapt to changing data statistics) so we set the forgetting factor λ to 1.

Note that the RLS update of Eq. (3) is very similar to the SGD update of Eq. (15) discussed below. The only difference is that the inverse feature covariance matrix $M_{k+1}$ replaces SGD scalar learning rate η. This more feature-tailored step size enables RLS to have a faster (single-epoch!) convergence and, importantly, the ability to recall previous class features. It is in this inverse feature covariance matrix M that much of Deep RCA's memory resides.

To modify the online, adaptive RLS algorithm for the task of model augmentation, we recognize that all potential future classes can simply be viewed as classes for which the online optimizer has yet to come across a positive training example. This viewpoint motivates the computation of a single null-class vector Δw, which encodes all the negative training class examples and is used to initialize new classes. Because this initialized weight vector already contains all the prior classes' negative feature examples, the new class weight vector can now be trained on just the positive examples associated with the new class. In this manner Deep RCA avoids having to train on previously seen negative training examples to implement optimal model augmentation. It also avoids the issues caused by the random new class weight vector initialization used in Progressive SGD.

There are several ways to compute the null-class vector Δw. One approach is simply to use the normal equation solution as seen in Eq. (4).

$$\Delta w = -\left(XX^T\right)^{-1} X^T T_{Neg} \tag{4}$$

Here the training label vector $T_{Neg}$ (of shape Ns×1) is set to all negative ones to indicate that all prior training samples have not included this class. Note that Deep RCA uses positive and negative 1's as the class labels instead of the common binary (0 or 1) one-hot encoded labels. This modification allows the negative feature examples to be observed and preserved in the null-class vector.

Computing Δw using Eq. (4) has the drawback that the feature data X for all prior classes, must be stored in order to initialize a new class. A recursive implementation for Δw avoids this drawback and can be computed as:

$$\Delta w_{k+1} = \Delta w_k + M_{k+1} x_{k+1} (T_{Neg} - x_{k+1} \Delta w_k) \tag{5}$$

where $T_{Neg}$ is again an Ns×1 matrix of negative one labels indicating that none of the examples correspond with any of the classes.

Intuitively, one can think of this initialization vector to be the projection into the space most opposite to the prior classes and where the initialization vector will have minimum interference with previous class vectors. It is from this insight that the name null-class vector was chosen. Thus, Deep RCA's null-class vector Δw provides a way of encoding negative class feature knowledge and its inverse feature covariance matrix M provides a way of preserving feature correlations. By using these two components, Deep RCA can avoid having to retrain an augmented model on data it has previously seen and the training process can be much more rapid and memory efficient.

The RCA algorithm can operate in three different stages. The first stage is the base model initialization. This stage computes the initial classification model based on what labeled class training data is available. This can be computed via the known equations (hereafter the "Normal Equation(s)"), as shown in Eq. (6) (Initialize inverse feature covariance) and (7) (Initialize Normal Equation Solution):

$$M_0 = \left(X_0^T X_0\right)^{-1} \tag{6}$$

$$w_0 = M_0 X_0^T T_0 \tag{7}$$

The RCA null-class vector is also initialized by assuming that all the training data are negative examples of a future class as per Eq. (3).

$$\Delta w_0 = -M_0 X_0^T T_0 \tag{8}$$

RCA can operate in a second, optional mode, that updates its model weights given additional training data but no new training classes. This update is the RLS update, again with the RCA null-class vector being computed, as shown in Eqs. (9) (Covariance Update), (10) (Model Update) and (11) (Null-Class Vector Update):

$$M_{k+1} = M_k - M_k x_{k+1}^T \left(1 + x_{k+1}^T M_k x_{k+1}\right)^{-1} x_{k+1}^T M_k \tag{9}$$

$$w_{k+1} = w_k + M_{k+1} x_{k+1} \left(t_{k+1}^T - x_{k+1}^T w_k\right) \tag{10}$$

$$\Delta w_{k+1} = \Delta w_k + M_{k+1} X_{k+1}^T (-X_{k+1} \Delta w_k) \tag{11}$$

The third operational RCA mode also called the RCA model extension step, occurs when training data for a new class arrives and the old model must be extended to accommodate this new class. In this stage, the old RCA model matrix $w_k$ (number of features F×number of old classes NbC) is augmented with a new class initialization vector $\Delta w_k$ of size F by 1, to form the new augmented model.

$$w_k = [w_k, \Delta w_k] \tag{12}$$

This new-class initialization vector $\Delta w_k$ is defined in a recursive implementation in Eq. (13).

$$\Delta w_{k+1} = \Delta w_k + M_{k+1} x_{k+1} (T_{Neg} - x_{k+1} \Delta w_k), \tag{13}$$

Here $T_{Neg}$ represents n Ns×1 matrix of negative one labels indicating that none of the preceding examples correspond with the new class.

This form of new class initialization allows the training to be explicitly independent of any old training data, but still contain information about negative training examples for the new class augmentation. This formulation does not require any storage of old training data for new class augmentation, which can be very beneficial when augmenting models on the edge with limited data storage. It also eliminates the random uncertainty in new class initialization used by Progressive SGD and is the second distinction from the progressive ELM approach mentioned earlier.

As shown in prior art FIG. 1(*b*), the Progressive SGD architecture is a pipeline consisting of a DNN used for feature extraction, followed by a fully-connected classifier layer. Images processed with this pre-trained feature extractor produce a new lower-dimensional feature data matrix, X of size number of samples (Ns), by feature vector dimension (F). This feature data matrix X can then be used as the standard input to a simple, fully-connected classifier that has a weight matrix of shape F by number of classes (NbC).

Prior art FIG. 1(*c*) zooms in on the class prediction layer of FIG. 1(*b*) and illustrates how a standard, fully-connected classifier can be modified for progressive learning. Specifically, it shows how the base classifier's old weight matrix (of size F×NbC) is augmented with a new class weight vector (F×1) to form a larger, multi-class, model. Observe that the class prediction score for this new model $X_{NsxF}w_{FxNbC+1}=T_{NsxNbC+1}$ has now also increased to accommodate the new number of classes where T, is of shape Ns×(NbC+1).

For the comparative analyses, the well-known SGD optimization update formula is shown in Eq. (14) where the updated weight vector $w_{k+1}$ is computed using its prior weights $w_k$ subtracted by the gradient of its loss function with respect to its weights, ∇L and multiplied by the hyperparameter, learning rate η.

$$w_{k+1}=w_k-\eta\nabla L. \tag{14}$$

Assuming the loss is the mean-square-error, ∇L can be replaced by $(t_{k+1}-x_{k+1}w_k)(-x_{k+1})$, where $t_{k+1}$ is the one-hot encoded, multi-class label vector for the k+1 training sample and $x_{k+1}$ is the k+1 training sample's feature vector. The overall update is $$w_{k+1}=w_k+\eta(x_{k+1})(t_{k+1}-x_{k+1}w_k). \tag{15}$$

To better understand the core RCA algorithm used in the Deep RCA process, a low-dimensional, linearly-separable example was generated using sklearn's "make_blobs" function. This process generated 2-D data points belonging to a different classes that were specified by a different mean and covariance. This blob data was then transformed by sklearn "normalize" function to produce a new set of class feature data that moved all the 2-D class data to a unit circle that had the mean value for all classes subtracted out. This low dimensional representation (essentially angular data around the unit circle) makes it easy to visualize the basic operations of a linear classifier and to intuitively understand more abstract concepts.

Figure 2A:
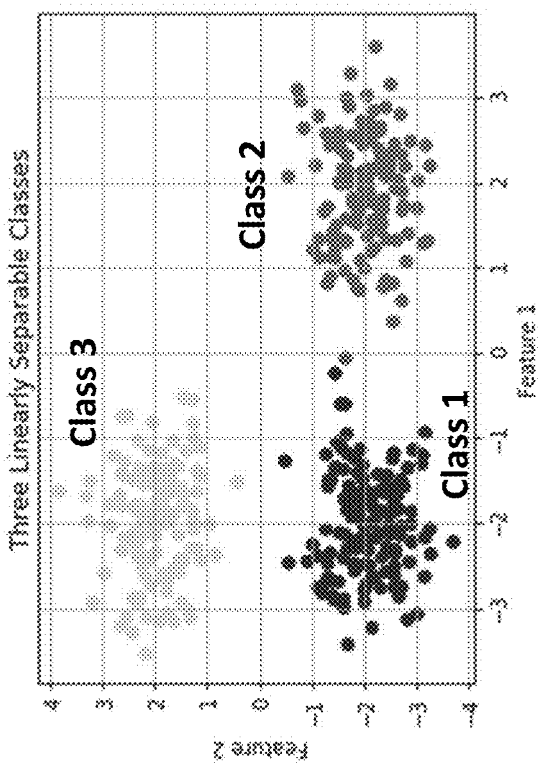
FIGS. 2(*a*) and 2(*b*) provide representations for visualizing classification score for a 2-class linear classifier.
Figure 2B:
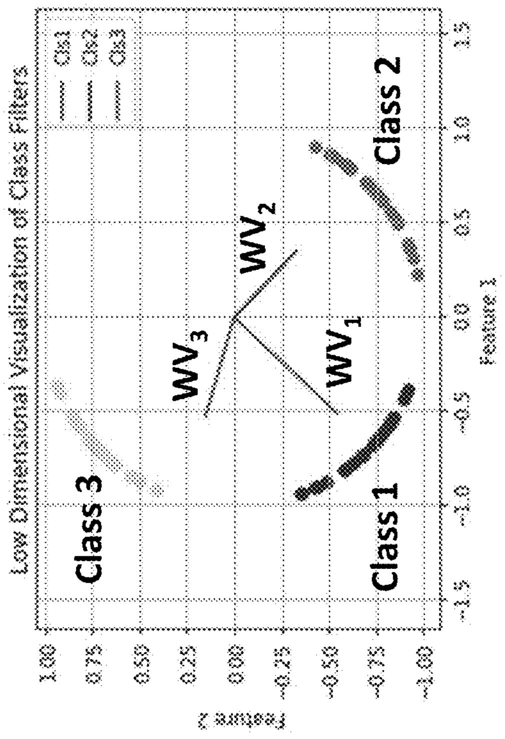

For example, FIGS. 2*a* and 2*b* show 3 linearly separable classes (FIG. 2*a*) that are transformed into essentially a 1-dimensional angular representation (FIG. 2*b*) using sklearn's normalization function although the 2-dimensional nature of the data (x & y) was maintained. The multimodal blob data was randomly sampled into train and test data sets. The training data was then used to train a (2-Feature×3-Class) linear classifier with the Normal Equations. Each column of that linear classification matrix represents the class feature weights. For example, the class-one weights are approximately [−1, −1], and so that class vector 'points' towards the class-1 data points.

This representation provides an easy way of visualizing the classification score as the projection of the class weights ($WV_1$, $WV_2$, $WV_3$) onto the samples features of a class (Class 1/Cls1, Class 2/Cls2, Class 3/Cls3). The projection with the highest score dictates classifiers decision. In this low dimensional, feature space one can easily see that the model has learned the three classes. Note however, that the $WV_3$ is not centered on the data cluster but rather is sufficiently close that the classification score works.

Figure 3A:
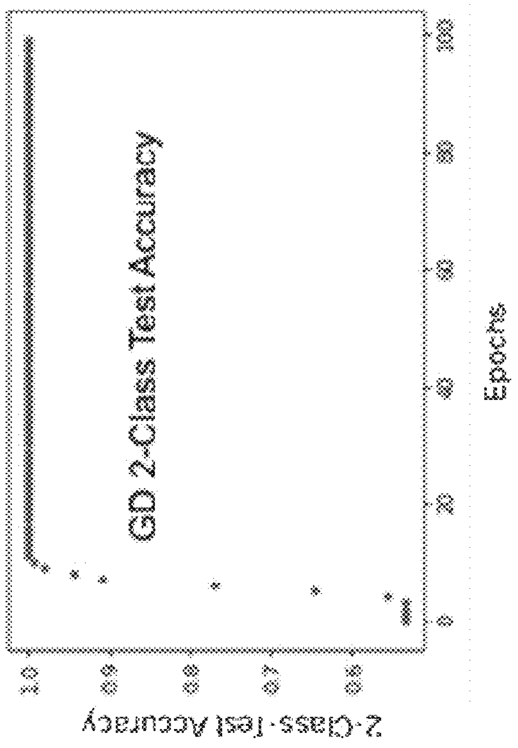
FIGS. 3(*a*) and 3(*b*) provide representations of classification accuracy and loss metric for 2-class linear classifier using prior art classifier.
Figure 3B:
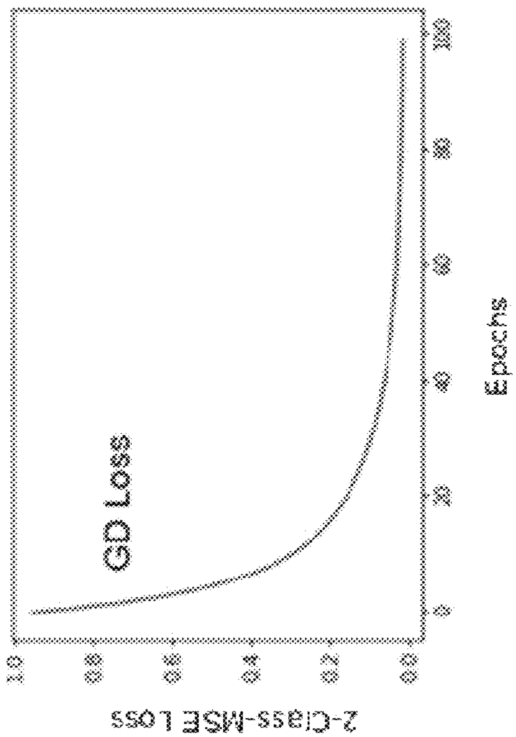

FIGS. 3*a* and 3*b* shows the rapid convergence and training of a 2-class linear classifier using the conventional iterative, gradient-descent (SGD), optimization procedure. The rapid increase in classification accuracy (in under 20 epochs) (FIG. 3*a*), and the rapid decline in the loss metric (FIG. 3*b*), indicate that gradient-descent optimization can quickly train this two class-classifier.

Figure 4A:
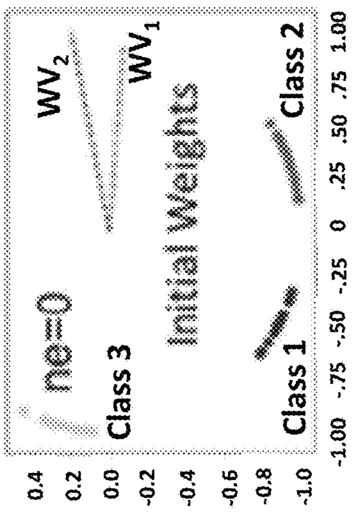
FIGS. 4(*a*), 4(*b*) and 4(*c*) provide representations for visualizing training of 2-class linear classifier trained using prior art process.
Figure 4B:
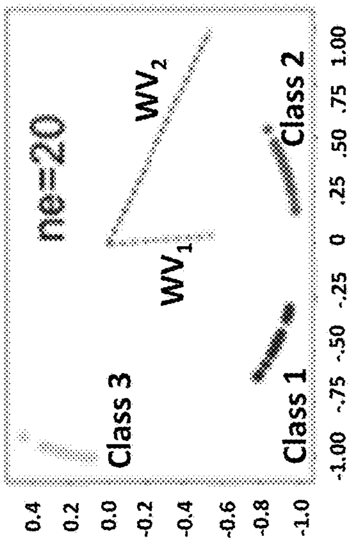
Figure 4C:
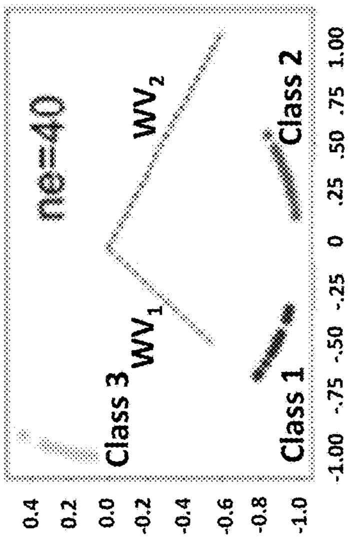

FIGS. 4*a*, 4*b* and 4*c* provide another way of visualizing this training process. FIG. 4*a* shows the random initialization for the 2-class weights shown by the vectors ($WV_1$, $WV_2$) for the class-1 and class-2 training classes. FIG. 4*b* shows how the training process has modified the weights so that now the model is successfully classifying both class-1 and class-2. This can be seen by estimating the projection score of a sample point onto the class weight vector, as well as by looking at the training accuracy at the $20^{th}$ training epoch. By the $40^{th}$ epoch, FIG. 4*c*, the weight vectors ($WV_1$, $WV_2$) for the two classes are clearly distinguishing themselves and generally point in the direction of their respective classes. Note however that the weight vectors still have not reached their optimum values at this point. This simple example is primarily included to document the fact that gradient descent algorithms can work effectively to train linear classifiers, when supplied training data representative of all model classes.

Figure 5:
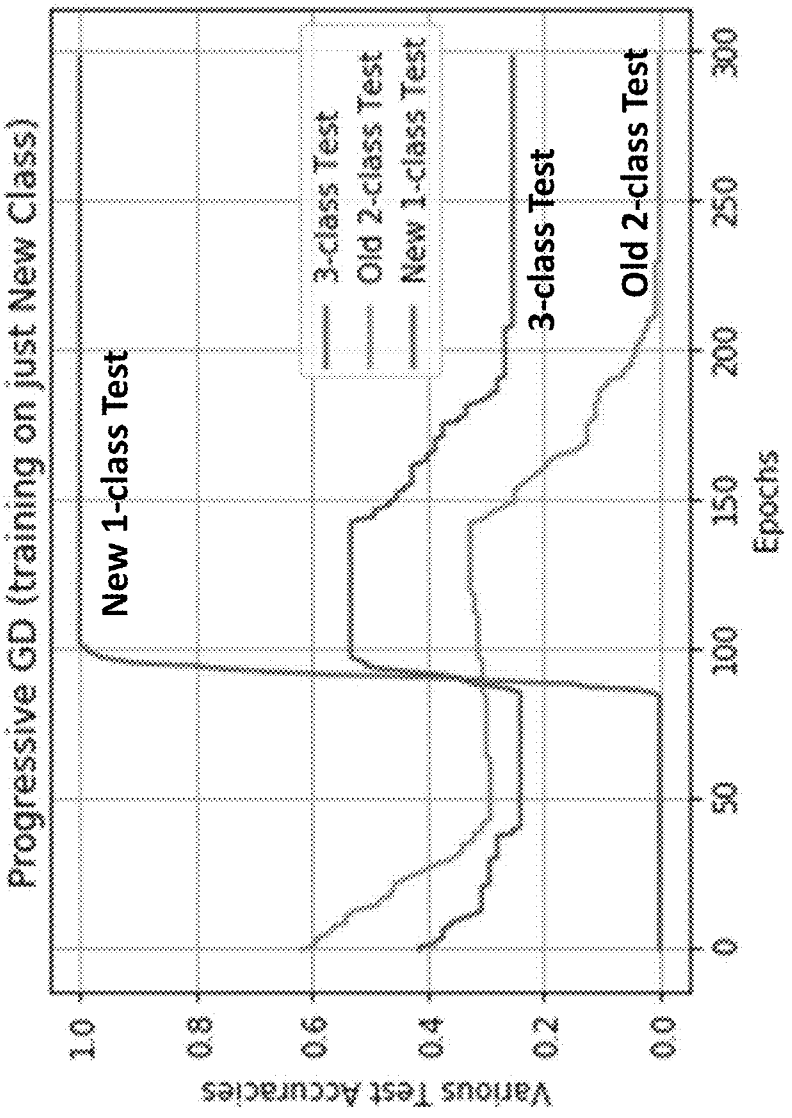
FIG. 5 shows various test accuracies of an augmented, 3-class model when trained using prior art process using only the 3-class data and first, random 3-class initial weight vector.

FIG. 5 Shows various test accuracies of an augmented model when trained using Progressive SGD and supplied with only the new class training data (class-3 data). The specific test accuracies include: the overall 3-class test set which contains test examples of all 3 classes; the old 2-class test set which consists of the previously learned 2 class test examples and the new 1-class test set, which consists of only new class test examples. FIG. 5 suggests that the augmented model 'forgets' its previous training on the prior two classes as it is augmented and trained with the new class three data, as is indicated by the rapid decline of the augmented model's performance on the old 2-class test data. FIG. 5 also shows that the augmented model can learn the new class weights as seen by the increase in test accuracy on the augmented class data. We can see the overall 3-class test initially degrades and then goes up again when it learns its new class weights and then slowly erodes to essentially one-class test accuracy (~0.3).

Figure 6A:
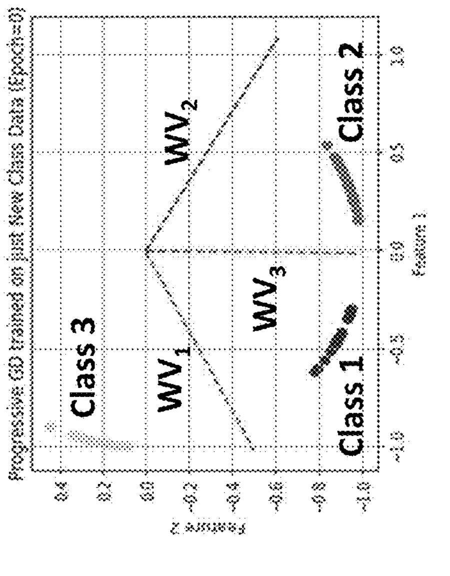
FIGS. 6(*a*), 6(*b*) and 6(*c*) provide representations for visualizing training of an augmented, 3-class linear classifier trained using prior art process using only the 3-class data and first, random 3-class initial weight vector.
Figure 6B:
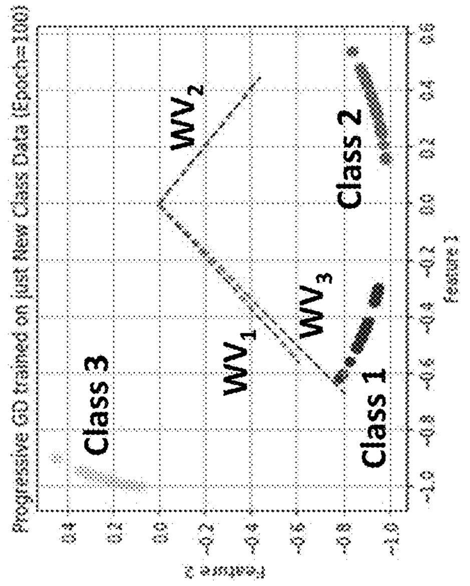
Figure 6C:
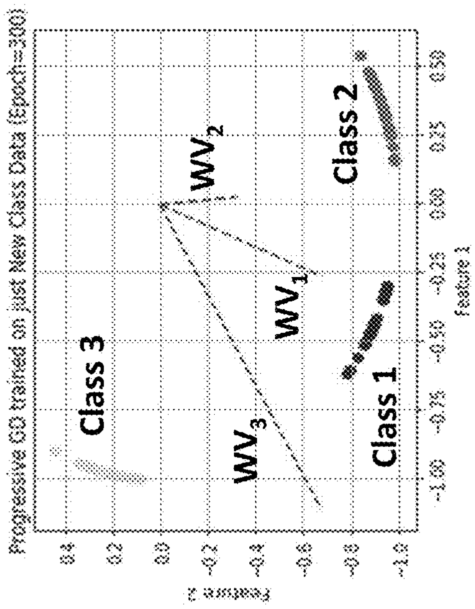

FIGS. 6*a*, 6*b* and 6*c* visualize the training process of FIG. 5 with the augmented model's weight vectors ($WV_1$, $WV_2$, $WV_3$). The augmented model is initialized with the old class weights (shown here as the $WV_1$ and the $WV_2$ weights that perfectly classified the first two classes) and a random initialization for the new 3rd class, $WV_3$. Note that this is a particularly poor 'random' initialization for the new class weights. Because of this poor initialization (stage 1, Epoch 0), the augmented model's accuracy for the old two classes is immediately dropped from 100% to about 60% with most of the errors incorrectly classifying the old classes as the new third class (FIG. 6*a*). As the training progresses (stage 2, Epoch 100) the new third-class weight vector ($WV_3$) slowly rotates towards its class-3 data and $WV_1$ rotates away from the class-3 data (FIG. 6*b*). Finally in (stage 3, Epoch 300) (FIG. 6*c*), the augmented model has learned that the world consists only of class-3 data, and all other class weights should reside in the null-space of the class-3 data. The old two class weight vectors continue to rotate around to be small and orthogonal to new class three data. This represents the model's new view of the world (that aligns with its training data), that all data should be classified as class-3, and that class 1 & 2 weights should always yield scores of 0 (i.e. be orthogonal to class-3).

The initialization of the new class training data in this example was particularly poor because it aligned and overlapped largely with the other two training classes. So, in the next example, we pick a better 'random' initialization for the 3rd class augmentation vector and see how that impacts its performance.

Figure 7:
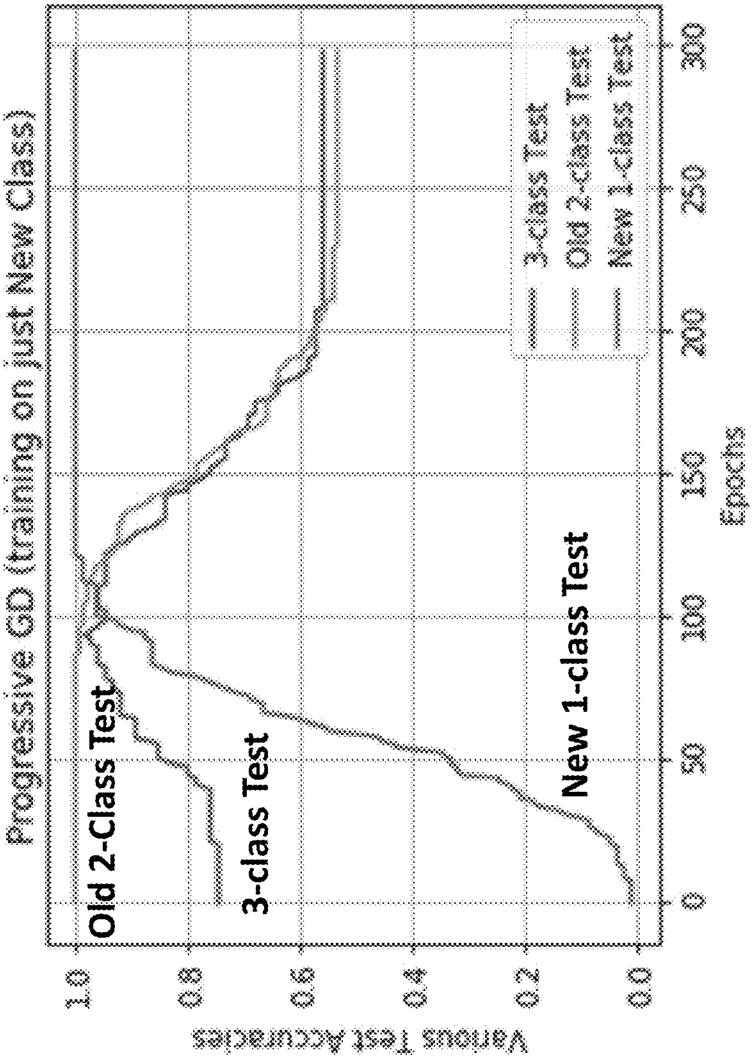
FIG. 7 shows various test accuracies of an augmented, 3-class model when trained using prior art process using only the 3-class data with different 3-class initial weight vector.

FIG. 7 repeats the above experiment, namely examining various test accuracies of an augmented model when it is provided a different and better 'random', initialization for its augmentation class weight vector. In this example, the augmented model again learns the new class weights and performs well on unseen, test data of this class (New 1-class Test). However, in this example, the random initialization augmentation vector did not interfere and project onto the old classes as much as in the previous example, so the augmented model maintains its high-classification accuracy on the two previously trained base-classes for longer (Old 2-Class Test). Then it too begins the process of unlearning the prior class features and modifying its weights so that two old classes lie orthogonal to the new class weight vector ensuring a zero score. The overall 3-class performance (3-class Test) peaks at around the 100-training epoch as the new class is learned and before the corrections are made to the old weights ensuring a zero score. However, it would be difficult to ensure that the SGD stops training at this point as its MSE and thus its performance objective is not yet achieved.

Figure 8A:
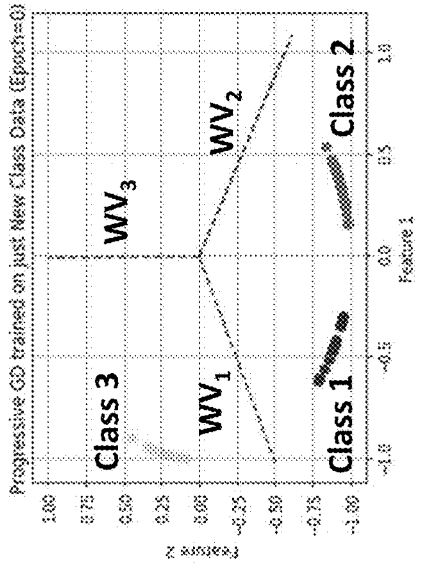
FIGS. 8(*a*), 8(*b*) and 8(*c*) provide representations for visualizing training of an augmented, 3-class linear classifier trained using prior art process using only the 3-class data with different 3-class initial weight vector.
Figure 8B:
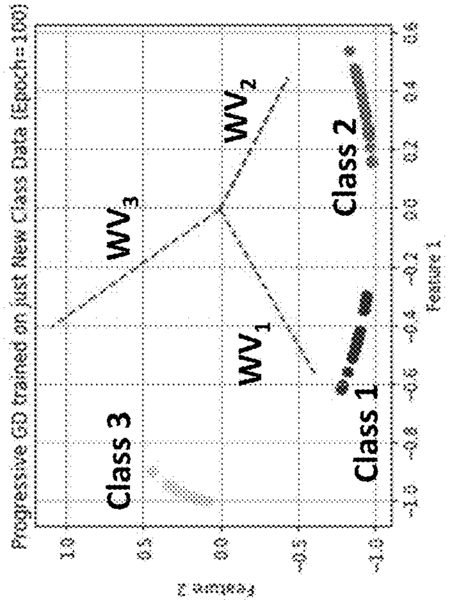
Figure 8C:
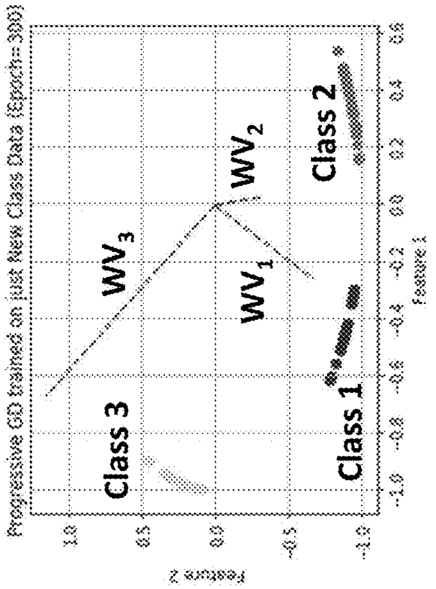

FIGS. 8*a*, 8*b* and 8*c* provide another visualization of this example of FIG. 7. Note in stage 1 the relatively good initialization for the new class (Class-3) in that the new augmentation class vector $WV_3$ does not point towards and misclassify the two base classes (Class-1 and Class-2). Thus, there is a relatively high 3-class classification accuracy starting in stage 1 (FIG. 8*a*). By stage 2, the model has adjusted its class weights to better deal with the new class data (FIG. 8*b*). Specifically, the class-1 weights ($WV_1$) have moved around closer to projecting on its (Class-1) data class and the new class weight vector (Class-2) has also rotated around to produce a higher score as it projects more accurately on the new class-3 data. However, by stage 3, the model has continued to adapt to its new world view, namely that all data is of class 3 and to ensure that the other classes score zero, their class weights must be modified by moving them closer to the orthogonal space of class-3 and shrinking their magnitude (FIG. 8*c*).

Figure 9A:
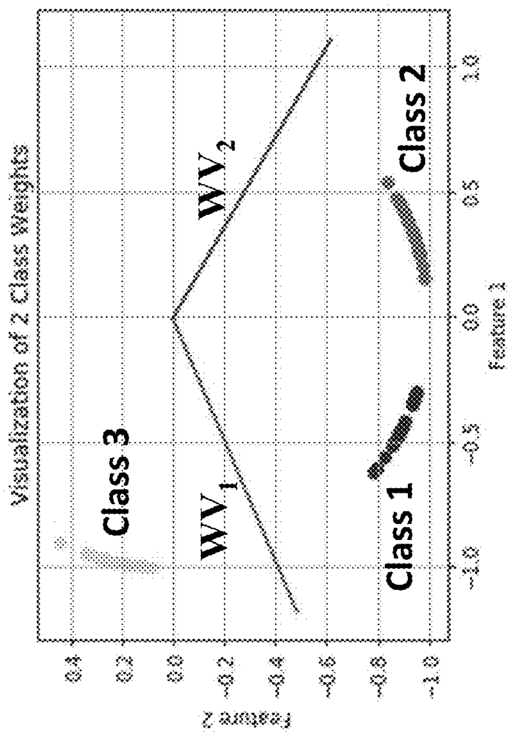
FIGS. 9(*a*) and 9(*b*) visualize class weights for 2-class and 3-class model when trained using prior art process using only the 3-class data and freezing the 2-class weights prior to training using only the 3-class data.
Figure 9B:
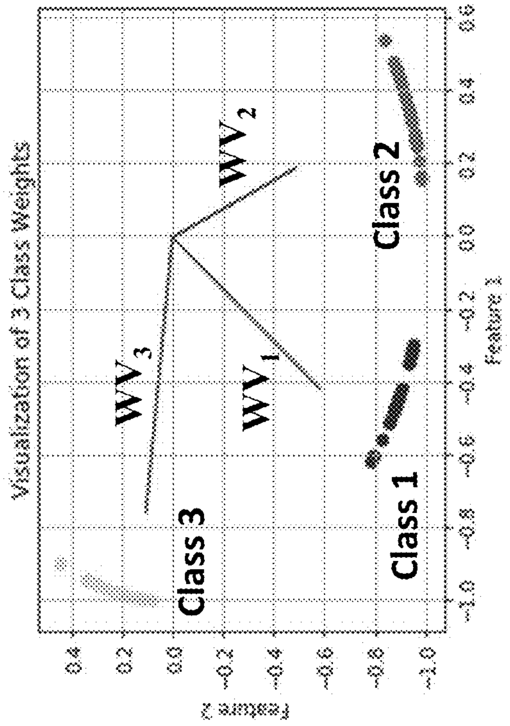

These prior examples have shown how the on-line optimization nature of SGD fails when provided only new class augmentation data. One might then wonder if it would not be better to freeze the prior class weights before training on the new data. FIGS. 9*a* and 9*b* show why freezing the prior class weights would result in sub-optimal performance. In FIG. 9*a*, the optimal MSE model weights for the two-class example are shown (Class-1 & Class-2). In FIG. 9*b*, the optimal MSE model weights for the 3-class example are shown. Note how now that the third class has been added the weight vector for class-1 ($WV_1$) has moved away from pointing in between class-1 and class-3 and now points more closely at its own class-1 data points (Class-1). This has the effect of reducing the chance of misclassifying class-3 data as class-1. This shows that the MSE optimal solution ideally modifies all class weight vectors when a new class is introduced. Thus, freezing the weights from the prior classes when augmenting a model's classes would likely lead to sub-optimal performance.

Figure 10:
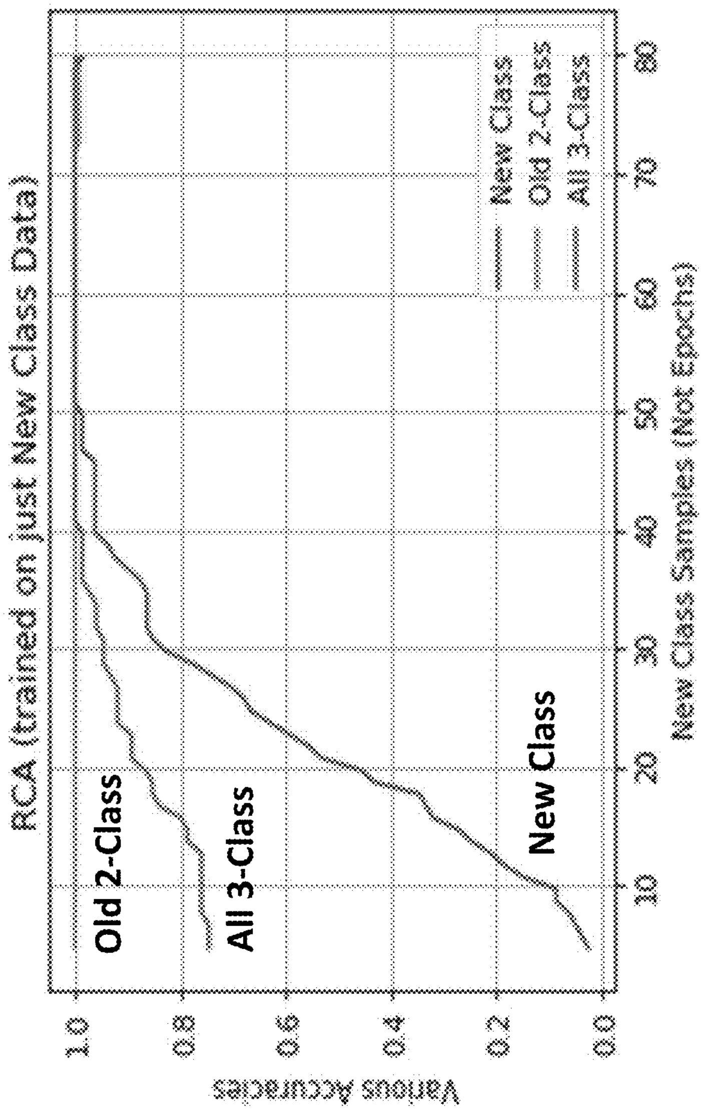
FIG. 10 shows various test accuracies of an augmented, 3-class model when trained using the RCA process of the present embodiments using only the 3-class data and predetermined null-class weight vector.

Now, FIG. 10 performs the same experiment, namely augmenting a 3rd class to a 2-class base model but this time using the RCA optimization. Note how all the various test accuracies increase with additional training. For RCA, the two-class test accuracy is maintained near 100% throughout the augmentation updates while the model is learning the new class. Thus, the overall RCA 3-class accuracy rises continually as new data is made available for training in stark contrast to the Progressive SGD.

Also, here the x-axis denotes the number of training samples in the new class as opposed to the number of training epochs (complete passes thru the training data) used in the previous examples with gradient descent. This shows that RCA can train more rapidly (i.e., with fewer data iterations) than SGD progressive learning which is an iterative procedure that can require 10's of epochs to complete the training.

Figure 11C:
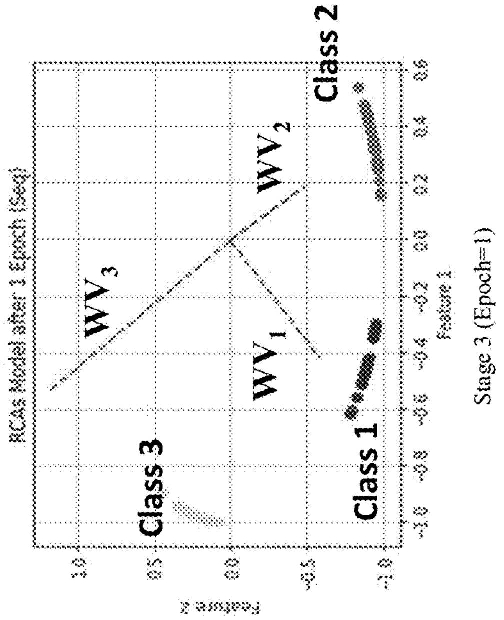
FIGS. 11(*a*), 11(*b*) and 11(*c*) provide representations for visualizing training of augmented, 3-class linear classifier trained using the RCA process of the present embodiments using only the 3-class data and predetermined null-class weight vector.
Figure 11B:
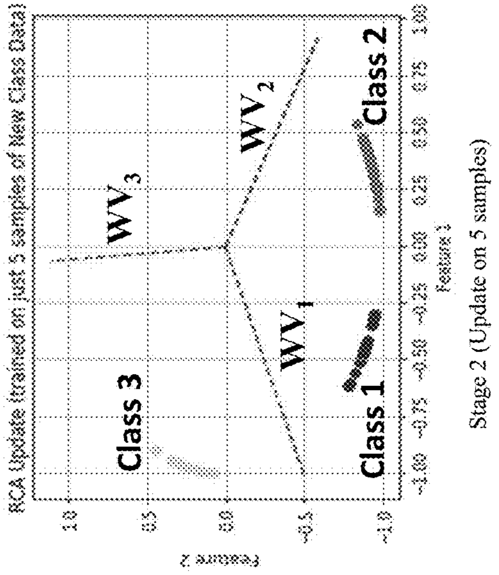
Figure 11A:
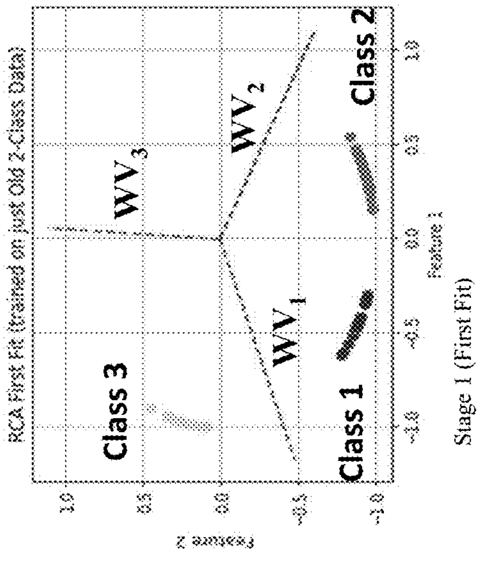

FIGS. 11*a*, 11*b* and 11*c* shows the RCA weight vectors at various points in its augmentation process. FIG. 11*a* shows the initialized RCA augmented model based on the output from the RCA first fit function that uses the training data from the first two classes to compute a two-class model, an inverse feature covariance matrix M, and a null-class augmentation vector $\Delta w$. The initialized weights $WV_1$ and $WV_2$ for RCA's class-1 and class-2 are shown. The null-class vector $\Delta w$ initializes the new class vector $WV_3$. Note how this initialization is not random but pre-determined and how it avoids interfering with the prior class weights. In FIG. 11*b*, the RCA first fit model is augmented and trained using 5 samples from the new class 3 data. Finally, after 1 epoch, RCA has successfully trained its weights to correctly classify all data classes FIG. 11*c*.

Figure 12A:
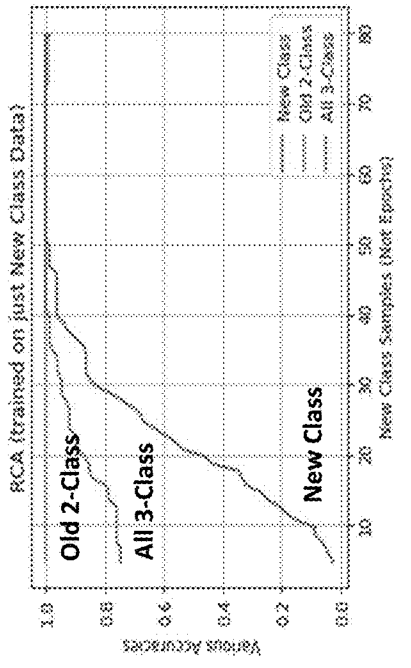
FIGS. 12*a*, 12*b* and 12*c* summarize and compare the performance of RCA (FIG. 12*a*) to prior art process given a good 'random' initialization (FIG. 12*b*) and prior art process given a poor 'random' initialization (FIG. 12*c*)
Figure 12B:
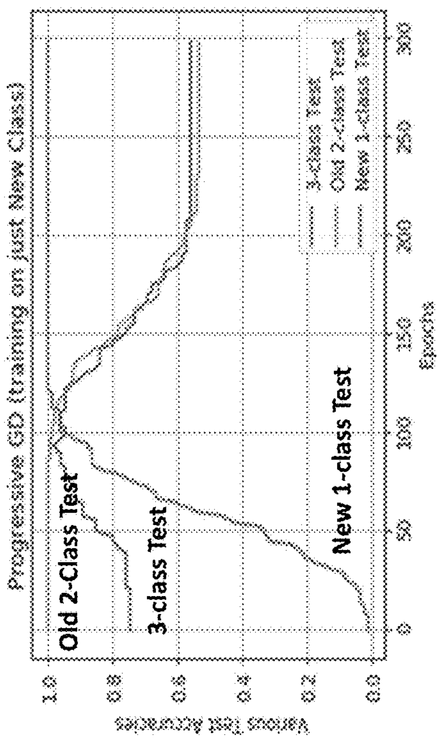
Figure 12C:
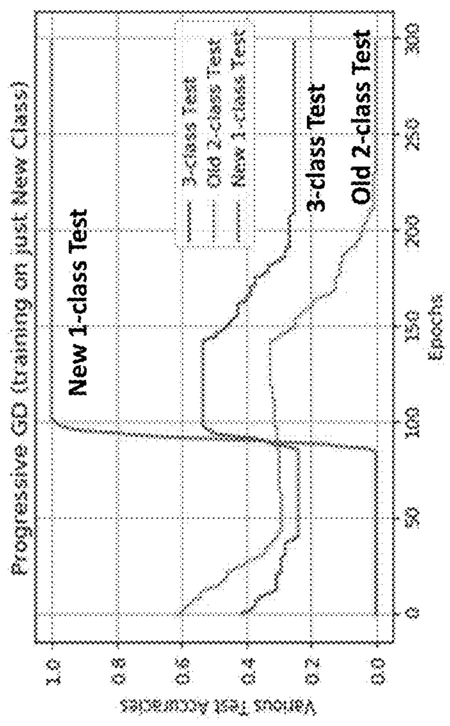

FIGS. 12*a*, 12*b* and 12*c* summarize and compare the performance of RCA (FIG. 12*a*) to Progressive SGD given a good 'random' initialization (FIG. 12*b*) and Progressive SGD given a poor 'random' initialization (FIG. 12*c*). Again, it shows that RCA can rapidly learn new classes (New Class) while maintaining its accuracy on the base-class models, even though it is only updating the weights of all 3-classes with the new class-3 data. This has ramifications of faster augmentation training times and less memory requirements. Progressive SGD on the other hand is vulnerable to poor augmentation weight initializations. Furthermore, even if a 'good' initialization vector is randomly selected (here 'good' is in the sense it does not immediately degrade the classification accuracy of the prior class weights), the SGD MSE metric when given just the new class data for model augmentation will incorporate false assumptions, namely that all data is now of class-3. This will result over-adapting the old model weights and result in poor performance. Of course, the fix is to train Progressive SGD using training data that reflects all training classes, but this results in increased training time and memory requirements.

An additional experiment using the MNIST data set further highlights the limitations of Progressive SGD; empirically demonstrating Progressive SGD's inability to effectively utilize previously trained class weights in a manner that preserves their own classification objectives when trained on only the new class data.

In this experiment, a pre-trained feature extractor network is first formed by training a DNN using the SGD optimization in the usual fashion. This network consisted of two convolutional layers followed by two fully connected layers for a total of 21K trainable parameters. Applying this classifier to test data yielded a 97% correct classification score.

This classification model is then used to create a feature extraction model by freezing the model weights up to its final classification layer. The extracted features for this model are 50-dimensional vectors. At this point we have a pre-trained feature extractor. The feature vectors for 9 classes are then extracted and used to train a new 9-class, base model classifier which has a weight matrix of shape F=50×NbC=9.

To test model augmentation, this base model is appended with an extra column to accommodate the new $10^{th}$ class. The new class column vector is initialized randomly and scaled to the average amplitude of the previously trained class weights. This augmented and initialized model is then trained using SGD on training data that only consisted of the new class data.

Figure 13:
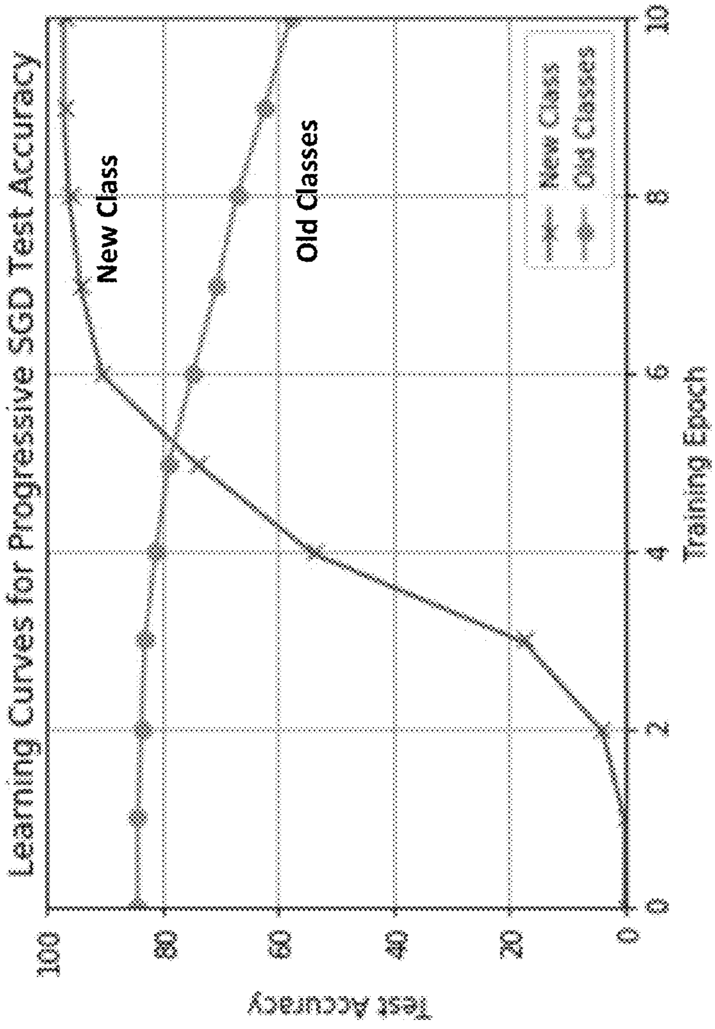
FIG. 13 shows various test accuracies of a multi-class model, augmented to add an nth class from the MNIST data set when trained using prior art process using only the nth-class data and first, random nth-class initial weight vector.

FIG. 13 displays the different test accuracies computed using test data containing just the 'New' $10^{th}$ class (New Class) and test data representing the 'Old' classes (Old Classes) and consisting of test samples from the previous 9 classes. FIG. 13 illustrates that during the augmentation training (when trained on just the new class data), the SGD optimizer teaches the network the new $10^{th}$ class but at the expense of the old classes' accuracy.

Observe that right at the start of the augmentation training, the old model class accuracy drops from 97% to 85%. This is caused by the random initialization of the new weight vector that inadvertently projects onto the old class weights. Thus, the random initialization of new class weight vector is seen to have the potential to cause strong interference with an old class vector and reduce its classification accuracy.

And regardless of the new class initialization, if the model is trained just on the new class data, the model's old class prediction accuracy will continue to degrade as the number of training epochs increases and as the new class is fit with ever greater efficiency and the old classes are increasingly forgotten.

The rationale behind this failure is that SGD optimizers have no memory. If the mini-batches contains only new class samples, the SGD optimizer will accumulate gradients that optimize only for that class and will update all its weights accordingly. This will cause the optimizer to ignore the classification performance of the previously learned classes while it learns the new class weights. Over time, this means the optimizer will modify the old, previously learned class weights so that they project minimally onto the new class features regardless of how this impacts their own classification accuracy.

Table 1 shows the classification accuracy for both the old and the new class test data after training over 50 epochs. The results indicate that the augmented classifier has completely forgotten its old classification accuracy (reduction from 97% down to 10%) after 50 epochs of augmentation training, even while it has aggressively learned the new class.

TABLE 1

| | Before Augmentation | After Augmentation | |
|---|---|---|---|
| Test Classes | Old Classes (1-9) | Old Classes (1-9) | New Class (only 10) |
| SGD Test Accuracy | 97% | 10% | 100% |

These observations demonstrate the key point that the generic Progressive SGD algorithm will fail to preserve previously learned classification objectives if the augmented model is trained on just the new class data.

Furthermore, it suggests that an optimizer that has no memory and random new class initialization weights is ill-suited to the task of continuous learning. This is because it forces the algorithm to continuously relearn all of its previously learned classes as it learns the new class weights. This requirement for a constant refresh of prior class training data increases the augmentation training time and the memory required to hold exemplars of all the training data.

For comparison, RCA progressive learning capabilities are also demonstrated on MNIST dataset. Using these features, an initial RCA 2-class base model $w_0$, is generated as described in the RCA base model initialization step. It returns a base model $w_0$, the inverse feature covariance matrix $M_0$, and the null vector $\Delta w_0$.

To test model augmentation, the current null vector $\Delta w_k$ is appended to the current classifier $w_k$, as described by RCA's model extension step. This augmented 3-class model is then trained using just the new $3^{rd}$ class data and its accuracy recorded on test data that includes all 10 MNIST classes. This class augmentation procedure is then repeated one class at a time to progressively include all 10 MNIST classes.

Figure 14:
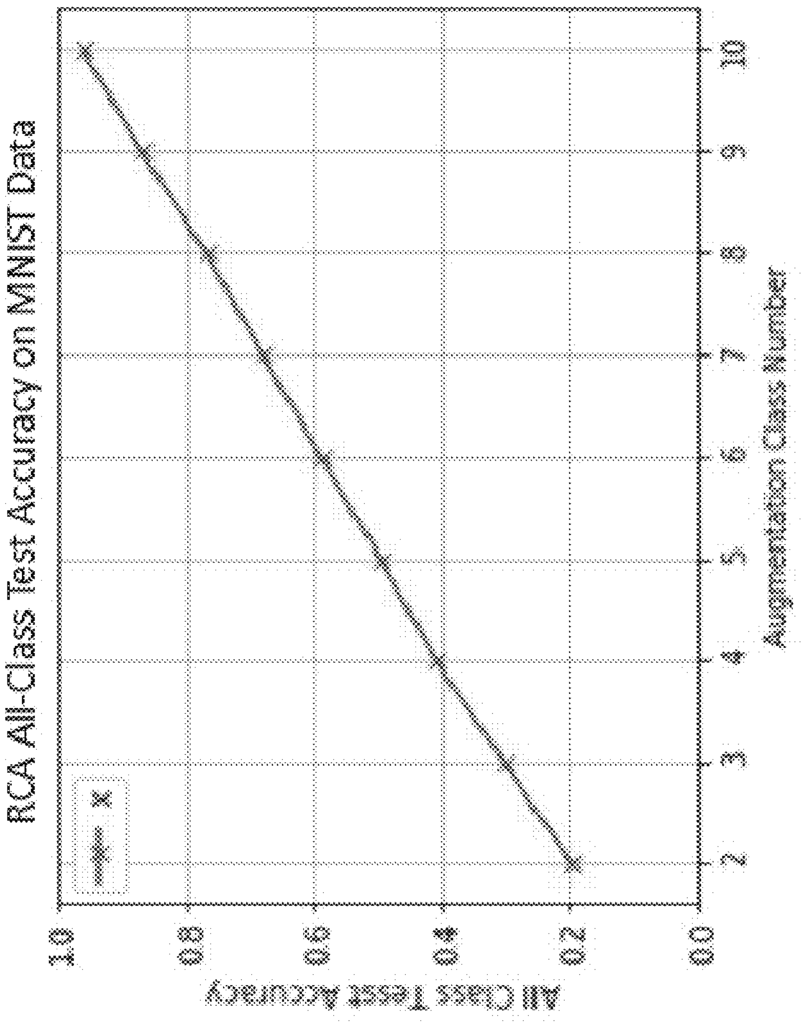
FIG. 14 shows various test accuracies of a multi-class model, augmented to add an nth class from the MNIST data set when trained using the RCA process of the present embodiments using only the nth-class data and predetermined null-class weight vector.

FIG. 14 shows the classification results of RCA augmentation over these 10 MNIST classes. After each new class augmentation, the model accuracy on the 10-class test data improves and by the last class augmentation, the model has reached a test accuracy of 97%. This experiment demonstrates that Deep RCA can successfully augment a classifier with new classes while using only the new class data for training.

Next, we repeat the experiment that was run using Progressive SGD above, but this time using the RCA implementation. As before, an initial 9-class base model is generated, along with RCA's inverse feature covariance and null-vector. This 9-class RCA model, along with training data for the new $10^{th}$ class are then supplied to RCA to augment the model to 10 classes. Table 2 summarizes the key steps used for the two approaches.

TABLE 2

| MNIST Augmentation Experiment Description |
|---|
| Progressive SGD:<br>Given an Existing 9-Class Progressive SGD Model:<br>1) Augment and Randomly Initialize New Class Weights<br>2) Train Using New Class Samples (1K Images)<br>3) Optimize MSE with SGD (50 Epochs)<br>RCA:<br>Given an Existing 9-Class RCA Model:<br>1) Augment & Initialize with Null-Class Vector<br>2) Train Using New Class Samples (1K Images)<br>3) Optimize MSE with RCA's modified RLS (1 Epoch) |

Figure 15:
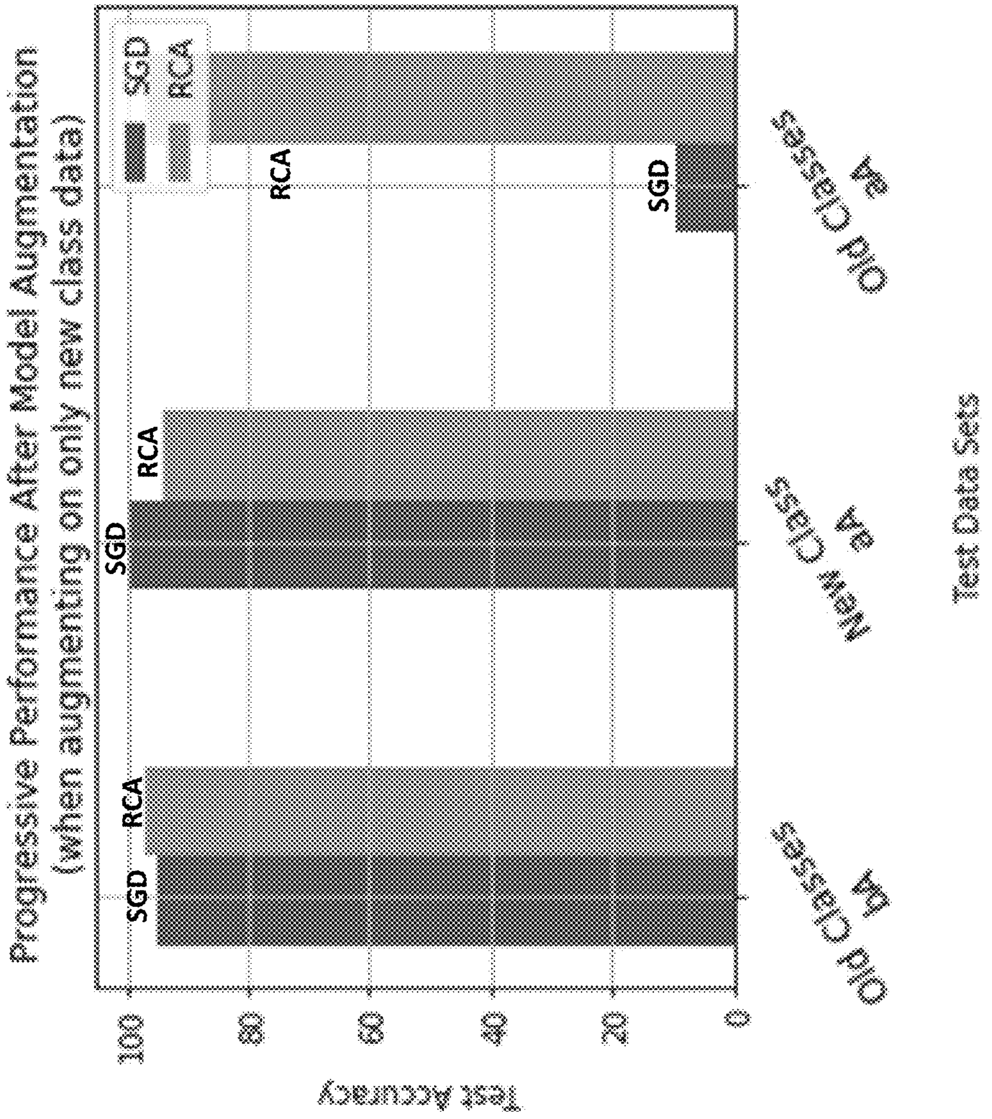
FIG. 15 shows the side-by-side comparison of the classification accuracies of both RCA and prior art processes, both before model augmentation (bA) and after (aA) model augmentation using data from the MNIST data set.

FIG. 15 shows the side-by-side comparison of the classification accuracies of both RCA and Progressive SGD, both before augmentation (bA) and after (aA) model augmentation. The bar-graph shows that after augmentation RCA was able to retain the 97% classification accuracy of the old classes while learning the new class, where Progressive SGD's old-class test accuracy decreased from 97% to 10% after 50 training epochs. The results highlight the fact that RCA can jointly optimize across both the old and the new classes when trained only on the new class data, while Progressive SGD focuses solely on learning the new class regardless of the cost to the old class accuracy.

Next, we compare the classification accuracy and augmentation time of RCA on the more complicated ImageNet data. This section also demonstrates RCA's ability to use a pretrained ResNet-32 model for feature extraction.

To start the experiment, a RCA 10-class model is trained on 10 ImageNette classes. Note that ImageNette classes are a subset of the well-known ImageNet data provided by FastAI as a more manageable size to quickly test new concepts. Each ImageNette class has approximately 1200 samples per training class and 100 samples per test class. This sample data is then fed through a ResNet-32 feature extractor to produce 512-dimensional feature vectors for each ImageNette class. A base 2-class model is initialized and then progressively trained using the ResNet-32 features generated for each of the classes.

Figure 16:
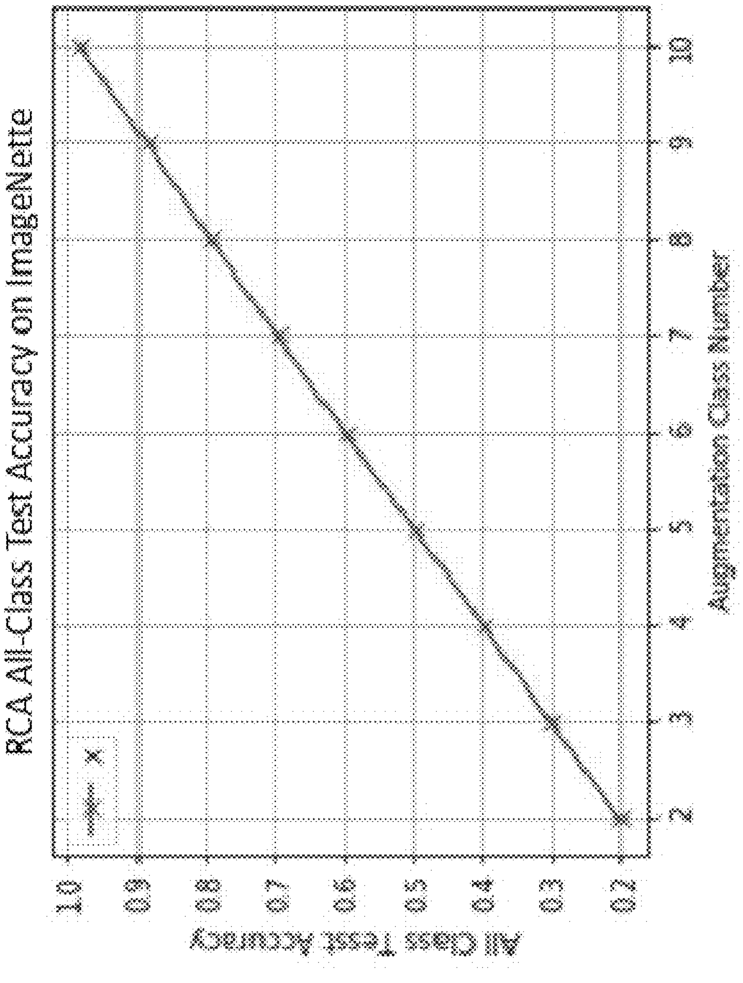
FIG. 16 illustrates the RCA's ability to progressively learn the 10 Image Net classes using just the new class training data.

FIG. 16 illustrates RCA's ability to progressively learn the 10 Image Net classes using just the new class training data. The result is a 10-class RCA model with a 98% test accuracy over data including all classes. Again, this example highlights RCA's ability to jointly optimize all class weights given just the new class data.

In the next experiment, a new 11th 'cat' class is augmented onto this 10-class RCA model. This generic 'cat' class data was taken from the fairly well-known dogs and cats Kaggle data set which was not part of the original ImageNet dataset on which the ResNet-32 feature extractor was trained. Note this augmentation extends the RCA model to a new class upon which its feature extractor was not explicitly trained and therefore also highlights the ability of RCA to use transfer learning's feature extraction as part of the model augmentation task.

Table 3 summarizes the results of this cat class augmentation experiment where RCA's classification and timing performance is compared to that of Progressive SGD. In this experiment, each algorithm is supplied a base 10-class model that it needs to augment with the additional cat class. Note that unlike the previous MNIST experiment, this time training images for all of the model's 11 classes are provided to the Progressive SGD optimizer, while RCA is given only the new 11th class cat images. This will allow Progressive SGD to maintain its accuracy across all classes but comes at the expense of training time and the memory required for storing all the old classes.

TABLE 3

| Cat Class Augmentation & Timing Experiment Description |
|---|
| Progressive SGD: |
| Given an Existing 10-Class Progressive SGD Model: |
| 1) Augment and Randomly Initialize New Class Weights |
| 2) Train Using Samples from All Classes (~13K Images) |
| 3) Optimize MSE with SGD (100 Epochs) |
| RCA: |
| Given an Existing 10-Class RCA Model: |
| 1) Augment & Initialize with Null-Class Vector |
| 2) Train Using New Class Samples (~0.5K Images) |
| 3) Optimize MSE with RCA's modified RLS (1 Epoch) |

Table 4 shows the augmentation test accuracy and update time for RCA compared to Progressive SGD. SGD's high test accuracy on both the old and new test classes confirm that when Progressive SGD is provided augmentation training data consisting of all of its model classes it can retain high classification accuracy over its old classes while learning the new class, albeit with longer training times.

TABLE 4

| | Test Accuracy After Augmentation | | | | |
|---|---|---|---|---|---|
| Test Classes | Old Classes (0-10) | New Class (Cat) | All Class | Update Time | Speed-Up |
| Progressive SGD 100 Epochs On All classes | 98% | 98% | 97% | 10.1 sec | |
| RCA 1 Epoch On New class | 98% | 99% | 98% | 0.1 sec | 100× Faster |

Note that Progressive SGD classification results were obtained after training for 100 epochs compared to RCA's 1 epoch. It was observed that Progressive SGD could obtain higher accuracy given substantially more training epochs than the 100 used, but that increased accuracy came at a cost of significantly more training time. The convergence rate was also seen to vary based on the new class vector's random initialization. Given these considerations and the fact that Progressive SGD's classification accuracy usually approached RCA's accuracy after 100 epochs, an SGD training time of 100 epochs was selected as a baseline for timing comparisons with the RCA approach.

The timing results shown in Table 4 were computed using Python's time module on a Dell Precision 7820 running Ubuntu 16.04 LTS with 156 GiB, Intel Xeon Silver 4112 CPU@2.60 GHz×16, and an NVIDIA GeForce GTX 1080 Ti/PCIe/SSE2 GPU. The results show that the RCA method trained its classifier 100 times faster than using a Progressive SGD approach and achieved similar or better all-class test accuracy. This significant speed up is attributed to the fact that SGD needs to operate over all 11 data classes (not just one) and needs to do so ~100 times (i.e. 100 epochs), not just once.

Table 5 shows the time required for the entire augmentation pipeline, including feature extraction. The results show that feature extraction dominates class augmentation time. For example, it took over a minute (62.5 sec) to generate the features for the 11 classes required for SGD, compared to the 2.4 seconds required to generate the new class features required for RCA.

TABLE 5

| Algorithm/Metric | Feature Time | Total Time | Speed-Up |
|---|---|---|---|
| Progressive SGD 100 Epochs 98% All Class Accuracy | 62.5 | 62.5 + 10.1 = 72.6 sec | |

TABLE 5-continued

| Algorithm/Metric | Feature Time | Total Time | Speed-Up |
|---|---|---|---|
| RCA @ 1 Epoch @ 98% All Class Accuracy | 2.4 | 2.4 + 0.1 = 2.5 secs | 29× Faster |

The combination of RCA's reduced feature extraction and classifier update times is seen to result in a 29× improvement over Progressive SGD's total augmentation pipeline. This is a difference between taking over a minute to learn a new class versus learning it in a few seconds, which can be important for time critical applications and is expected to grow as the number of base-model classes increases beyond ten. In general, the speed up ratio is seen to be roughly proportional to the ratio of the new class training examples versus the number of old class training examples. These timing experiments support near real-time class augmentation capabilities for large DNN classifiers.

To further test the new Deep RCA concept (per general architecture of FIG. 1), we built a feature extractor using the principals of deep CNN to transform raw image data into linearly separable features. For this particular test case, Deep RCA progressive learning capability is demonstrated on a data set containing 20 different vehicle classes of magnitude synthetic aperture radar (SAR) data from the MAD98 data set.

As mentioned above, Deep RCA requires a deep-neural-network feature extractor that can transform the raw high-dimensional images into a lower dimensional set of features upon which we can run the progressive RCA algorithm. This network can be a publicly available, architecture, (e.g. VGG16 or ResNet32) that is fine-tuned for SAR classification and whose lower layers are then used for feature extraction or a custom model. For the embodiment described herein, a custom feature extraction model was developed to succinctly capture the features of this type of SAR imagery.

Figure 17:
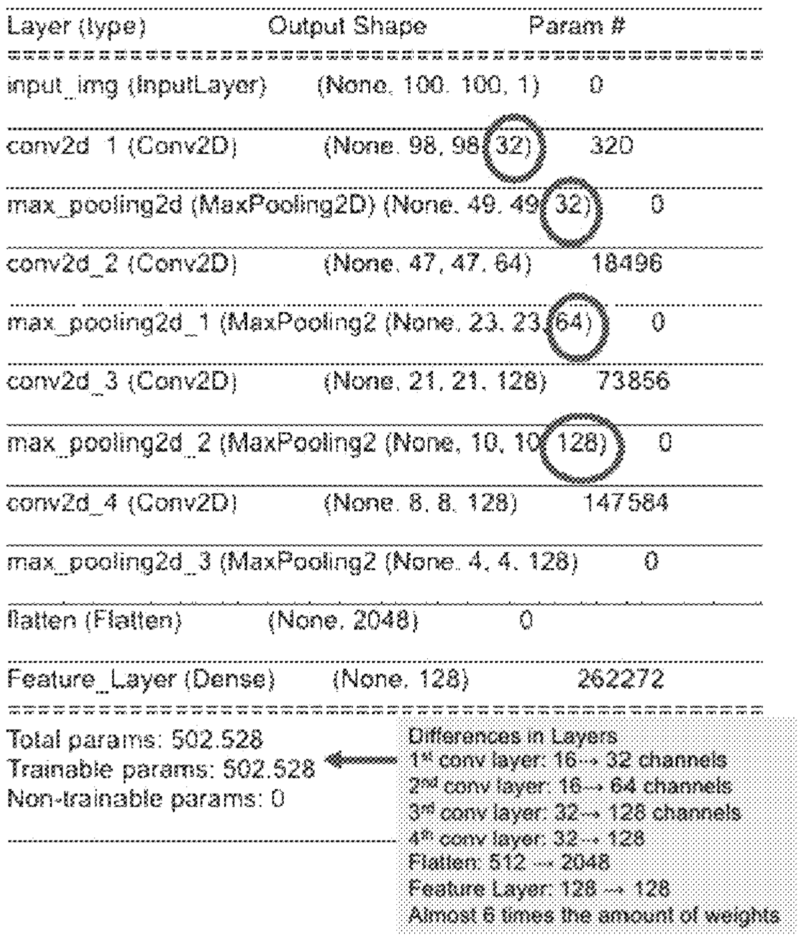
FIG. 17 illustrates the model architecture used for the feature extractor against the MAD98 data set in an embodiment herein.

Specifically, the feature extractor was trained on MAD98 SAR image chips of size 100×100. As shown in FIG. 17, the model architecture consisted of 4 layers, each comprised of a 3×3 convolutional kernel followed by a 2×2 max-pooling kernel. The layers respectively had channel dimensions of size 32, 32, 64, and 128. These 4 convolutional layers were followed by a flattening layer, which fed a fully connected layer that transform an image input into a 128-dimensional feature vector. This feature vector is then passed to the final, fully connected layer that yielded the prediction scores for the 20 classes. The model's loss was defined as mean-square-error and its weights trained using the Ada-Delta optimization method. Once this MAD98 model is trained, its last prediction layer was removed to expose a feature-extraction model, in a similar fashion to many transfer learning approaches.

Deep RCA uses this pre-trained feature extractor to sequentially process images to generate the features that will be fed into the RCA framework. The experimental results shown here are based on progressively growing an initial 2-class base model up to 20 classes. The initial base-model, along with its inverse covariance matrix $M_0$, is calculated using the Normal Equations on the 2-class training data, as described above. A new class augmentation vector is then computed for each new class introduced as described by Eq. (13) and its weights augmented as a column to the prior classes weight matrix. After the model is augmented, it uses the new augmentation class data to update the weights of all classes with the standard online RLS algorithm(s) in Eqs. (9) and (10) and as described above.

Figure 18:
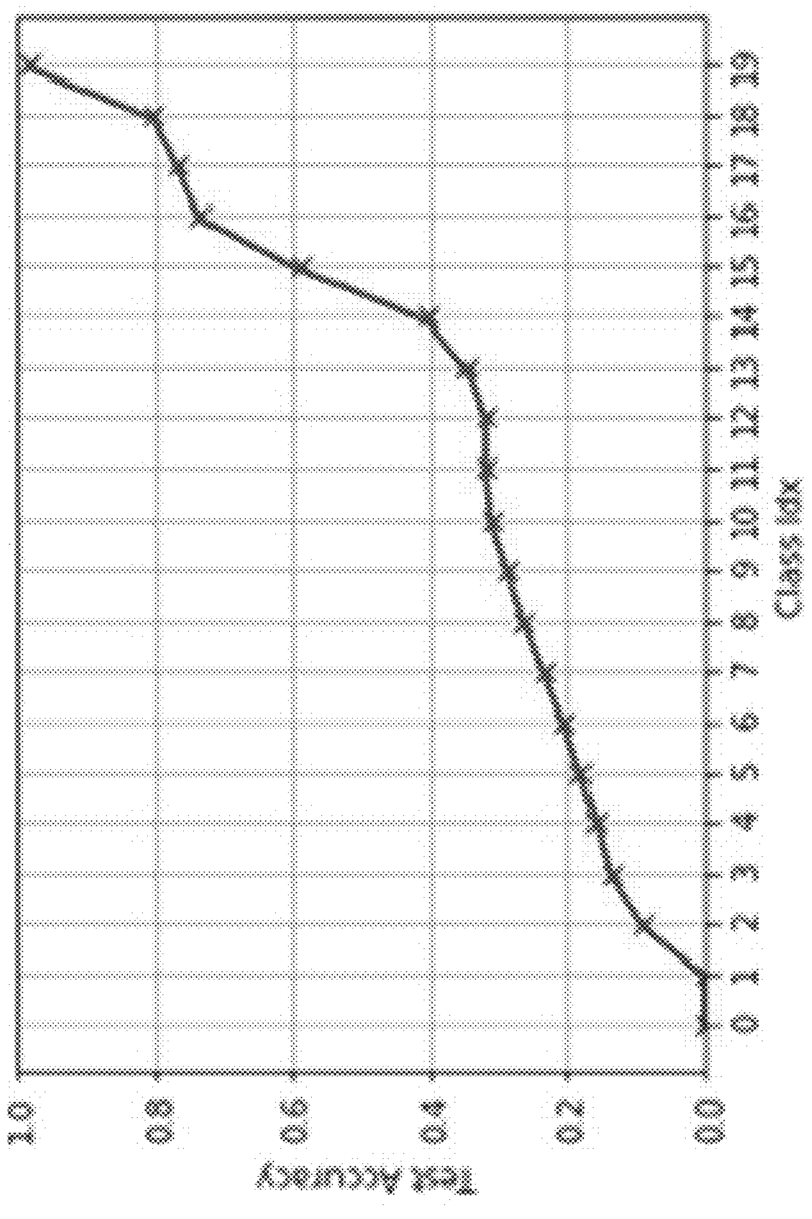
FIG. 18 shows the measured 20-class test accuracy as a function of the class augmentation index as a result of applying RCA during class augmentation.

FIG. 18 shows the results of this experiment. Specifically, it shows the measured 20-class test accuracy as a function of the class augmentation index. Note the 20-class test accuracy measures the RCA model's accuracy over a data set containing all 20 classes, even though the progressive model has not been trained on all the classes until it reaches the 19th class index. For example, this is the reason that class index 5 has only ~20% test accuracy even though the model has close to 100% test accuracy on those classes. Note the unequal increases in test accuracy, as a function of class, are caused by the unequal distribution of the classes in the test data. For example, the large increase from class 14 to class 15 is because the test data contains more class 15 vehicles, reflecting its overall higher class percentage. Also note that the FIG. 18 does not indicate (i.e. they are shown as zeros) the test accuracy for the base model consisting of the first two classes (0 and 1 indices). However it was recorded that the base model scored just under 0.1 (or 10%) test accuracy, which closely represents the portion of those two classes out of the full 20 classes).

These results further demonstrate that the new Deep RCA algorithm can progressively learn new classes on top of its old classes while training on only new class training data. This ability to remember old class features enables it to augment a model more rapidly in comparison to other progressive techniques that require access and computation on all the previous training classes.

A key performance metric for Deep RCA algorithm is the training time required to learn new classes. Therefore, Deep RCA's progressive augmentation time will be compared first to a traditional approach that uses no progressive learning or feature extraction and second to the previously described Progressive SGD approach.

To create the baseline timing comparison, a 20-class model was built from scratch on the MAD98 SAR data. The time required to train the full 20-class MAD98 model, non-progressively, over 30 epochs and reach a validation accuracy of 99.13% was 171.0 seconds. The full MAD98 model had the same structure as the layers described earlier to generate a deep CNN feature extractor, but with the prediction layer preserved.

To create the progressive learning timing comparisons, a 19-class, Progressive SGD model was initialized and the time it took to augment a new $20^{th}$ class was measured to be 3.5 seconds. This augmentation time included the time it took to pass the necessary training images thru the feature extractor, as well as the time it took to compute and update its classifier model, but not the time required to initially train the feature extractor.

The time it took Deep RCA to augment a new class onto a 19-class base model was measured to be ~0.1 seconds. This augmentation time also included the time it took to pass the necessary training images thru the feature extractor and to compute and update its prediction model. Note this measurement was at the limit of timing accuracy for our measurement method which does not reliably estimate timing below ~0.1 seconds. Therefore, we are unable to measure RCA update speed independent of the feature extraction step.

These timing experiments showed that Deep RCA could augment a 19-class model to a 20-class model 1700× faster than retraining a 20-class model from scratch. Furthermore, the Deep RCA method showed a 35× augmentation time speed up over the current Progressive SGD technique. These key timing findings are summarized in in Table 6.

TABLE 6

| Timing Results | Training Time (sec) | Deep RCA Speed-Up |
| --- | --- | --- |
| Deep RCA | 0.1 | N/A |
| Non-Progressive Baseline | 171.0 | 1700× Faster |
| LMS Progressive | 3.5 | 35× Faster |

These experiments confirm that progressive learning methods, particularly those that incorporate transfer learning techniques, can have a huge impact on the time required to augment new classes. Moreover, these results demonstrated that the new Deep RCA progressive learning approach can offer further reductions in augmentation times when compared to a Progressive SGD implementation. This is primarily because Deep RCA only requires the new class training data to optimally augment its model and only requires training over a single epoch. In contrast, techniques such as Progressive SGD, require training on all classes during model augmented over multiple epochs. This has large implications for their respective augmentation time.

It is submitted that one skilled in the art would understand the various computing environments, including computer readable mediums, which may be used to implement the methods described herein. Selection of computing environment and individual components may be determined in accordance with memory requirements, processing requirements, security requirements and the like. It is submitted that one or more steps or combinations of step of the methods described herein may be developed locally or remotely, i.e., on a remote physical computer or virtual machine (VM). Virtual machines may be hosted on cloud-based IaaS platforms such as Amazon Web Services (AWS) and Google Cloud Platform (GCP), which are configurable in accordance memory, processing, and data storage requirements. One skilled in the art further recognizes that physical and/or virtual machines may be servers, either stand-alone or distributed. Distributed environments many include coordination software such as Spark, Hadoop, and the like. For additional description of exemplary programming languages, development software and platforms and computing environments which may be considered to implement one or more of the features, components and methods described herein, the following articles are referenced and incorporated herein by reference in their entirety: Python vs R for Artificial Intelligence, Machine Learning, and Data Science; Production vs Development Artificial Intelligence and Machine Learning; Advanced Analytics Packages, Frameworks, and Platforms by Scenario or Task by Alex Cistrons of Innoarchitech, published online by O'Reilly Media, Copyright InnoArchiTech LLC 2020.

The invention claimed is:

1. A computer-implemented process for augmenting a classification model for classifying received data into a correct class, comprising:

augmenting an initial classification model having n classes trained on old class data to include a new class c and computing a null class weight vector for the new class c;

initializing training of an augmented classification model having n+c combined classes on training data consisting solely of new training data to new class c, wherein a classification accuracy of the n classes is maintained after training the augmented classification model on only the new class c training data, wherein the received data and the training data are high dimensional data; and further wherein, a neural network transforms the training data into linearly separable features prior to training the augmented classification model.

2. The computer-implemented process according to claim 1, wherein the received data and training data are image data.

3. At least one non-transitory computer-readable medium storing instructions that, when executed by a computer, perform a method for augmenting a classification model for classifying received data into a correct class, comprising:

augmenting an initial classification model having n classes trained on old class data to include a new class c and computing a null class weight vector for the new class c;

initializing training of an augmented classification model having n+c combined classes on training data consisting solely of new training data to new class c, wherein a classification accuracy of the n classes is maintained after training the augmented classification model on only the new class c training data wherein the received data and training data are non-linear, high dimensional data;

further including instructions for transforming the received data and the training data by a neural network into linearly separable features prior to training the augmented classification model.

4. The at least one non-transitory computer-readable medium according to claim 3 further including instructions wherein the received data and training data are image data.

5. A computer-implemented process for augmenting a classification model for classifying received non-linear, high dimensional data into a correct class, comprising:

a neural network for transforming non-linear, high dimensional data training data into linearly separable features prior to training an initial classification model having n classes;

augmenting an initial classification model having n classes trained on old class data to include a new class c and computing a null class weight vector for the new class c; and initializing training of an augmented classification model having n+c combined classes on training data consisting solely of new training data to new class c, wherein a classification accuracy of the n classes is maintained after training the augmented classification model on only the new class c training data.

* * * * *